United States Patent
Pike et al.

(10) Patent No.: US 7,141,545 B2
(45) Date of Patent: Nov. 28, 2006

(54) COMPOSITIONS AND METHODS FOR TREATING ARTICULAR CARTILAGE DISORDERS

(75) Inventors: Marilyn C. Pike, Lincoln, MA (US); Grushenka H. I Wolfgang, Oakland, CA (US); Sharon A. Chen, Mountain View, CA (US); Ralph M. Owen, Petaluma, CA (US); Lynn B. Seely, Burlingame, CA (US); Hans-Peter Guler, Rye, NY (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 371 days.

(21) Appl. No.: 10/199,449

(22) Filed: Jul. 19, 2002

(65) Prior Publication Data
US 2003/0134792 A1 Jul. 17, 2003

Related U.S. Application Data

(63) Continuation of application No. 09/285,554, filed on Apr. 2, 1999, now abandoned.
(60) Provisional application No. 60/080,683, filed on Apr. 3, 1998.

(51) Int. Cl.
*A61K 38/16* (2006.01)
*A61K 38/18* (2006.01)
(52) U.S. Cl. ............................. 514/12; 514/2
(58) Field of Classification Search ............ 514/2, 514/12
See application file for complete search history.

(56) References Cited

U.S. PATENT DOCUMENTS

| 4,642,120 A | 2/1987 | Nevo et al. |
| 5,206,023 A | 4/1993 | Hunziker |
| 5,374,620 A | 12/1994 | Clark et al. |
| 5,407,913 A | 4/1995 | Sommer et al. |

(Continued)

FOREIGN PATENT DOCUMENTS

EP 0 434 625 B1 4/1995

(Continued)

OTHER PUBLICATIONS

Caldwell et al., "A Safety Tolerability and Pharmacokinetic Study of Intra-Articular Recombinant Human Insulin-Like Growth Factor (rhIGF-I) in Patients with Severe Osteoarthritis (OA) of the Knee," Abstract 941, Abstract Supplement 2000, American College of Rheumatology 64th Annual Scientific Meeting and Association of Rheumatology Health Professionals 35th Annual Scientific Meeting, Oct. 29-Nov. 2, 2000, Philadelphia, Pennsylvania, p. S223, American College of Rheumatology, Atlanta, Georgia.

(Continued)

*Primary Examiner*—Michael Borin
(74) *Attorney, Agent, or Firm*—Leslie T. Henry; Susan Abrahamson; Alisa A. Harbin

(57) ABSTRACT

A method for treating mammalian articular cartilage disorders, more particularly osteoarthritis, and trauma-related cartilage injuries using insulin-like growth factor I (IGF-I) is provided. The method comprises increasing the amount of IGF-I at the diseased or injured articular site to a therapeutically effective level that is capable of maintenance and/or regeneration of cartilage, which is beneficial to the long-term treatment of osteoarthritis and trauma-related injuries to cartilage tissues. In one embodiment of the invention, single doses of at least 0.01 mg of pharmaceutically effective IGF-I are administered intermittently such that the duration of time off of therapy is greater than the time on therapy, more preferably with a frequency of administration of about once per week or less.

40 Claims, 1 Drawing Sheet

U.S. PATENT DOCUMENTS

| | | | |
|---|---|---|---|
| 5,444,047 | A | 8/1995 | DiPasquale |
| 5,597,802 | A | 1/1997 | Clark et al. |
| 5,643,867 | A | 7/1997 | Maack et al. |
| 5,655,546 | A | 8/1997 | Halpern |
| 5,712,249 | A | 1/1998 | Halloran |
| 5,728,676 | A | 3/1998 | Halloran |
| 5,843,899 | A | 12/1998 | Halloran |
| 5,853,746 | A | 12/1998 | Hunziker |
| 5,942,499 | A * | 8/1999 | Radomsky ............... 514/54 |
| 6,645,945 | B1 * | 11/2003 | Radomsky et al. ......... 514/54 |

FOREIGN PATENT DOCUMENTS

| | | |
|---|---|---|
| EP | 0 742 228 A1 | 11/1996 |
| JP | 2268190 | 11/1990 |
| JP | 6312931 | 11/1994 |
| WO | WO 92/13565 | 8/1992 |
| WO | WO 94/12219 | 6/1994 |
| WO | WO 95/32003 | 11/1995 |
| WO | WO 96/02565 A1 | 2/1996 |
| WO | WO 96/07424 | 3/1996 |
| WO | WO 96/37216 | 11/1996 |
| WO | WO 98/00183 | 1/1998 |
| WO | WO 99/08728 | 2/1999 |
| WO | WO 99/24062 A1 | 5/1999 |

OTHER PUBLICATIONS

Chen et al., "Pharmacokinetics of Recombinant Human Insulin-Like Growth Factor I (rhIGF-I) and a Slow-Release Formulation of rhIGF-I in a Dog Model of Osteoarthritis," Abstract 3390, American Association of Pharmaceutical Scientists Annual Meeting, Nov. 15-18, 1998, San Francisco, California.

Chevalier et al., "Production of Binding Proteins and Role of the Insulin-Like Growth Factor 1 Binding Protein 3 in Human Articular Cartilage Explants," *British Journal of Rheumatology*, 1996, pp. 515-522, vol. 35, British Society for Rheumatology.

*Chiron News*, "Chiron Concludes rhIGF-I Osteoarthritis Clinical Development Program," Press Release, Jul. 25, 2000.

Doré et al., "Human Osteoarthritic Chondrocytes Possess an Increased Number of Insulin-Like Growth Factor 1 Binding Sites But Are Unresponsive to Its Stimulation," *Arthritis and Rheumatism*, 1994, pp. 253-263, vol. 37(2), American College of Rheumatology, USA.

Fernihough et al., "Local Disruption of the Insulin-Like Growth Factor System in the Arthritic Joint," *Arthritis and Rheumatism*, Sep. 1996, pp. 1556-1565, vol. 39(9), American College of Rheumatology, USA.

Frisbie et al., "Insulin-Like Growth Factor 1 and Corticosteroid Modulation of Chondrocyte Metabolic and Mitogenic Activities in Interleukin 1-Conditioned Equine Cartilage," *American Journal of Veterinary Research*, 1997, pp. 524-530, vol. 58(5), College of Veterinary Medicine, Cornell University, USA.

Guler et al., "Recombinant Human Insulin-Like Growth Factor 1 Stimulates Growth and Has Distinct Effects on Organ Size in Hypophysectomized Rats," *Proceedings of the National Academy of Sciences of the USA*, 1988, pp. 4889-4893, vol. 85, Medical Sciences, Zurich, Switzerland.

Lloyd et al., "Relation Between Insulin-Like Growth Factor-1 Concentrations, Osteoarthritis, Bone Density, and Fractures in the General Population: The Chingford Study," *Annals of the Rheumatic Diseases*, 1996, pp. 870-874, vol. 55, Extended Reports.

McAlindon et al., "Levels of Insulin Related Growth Factor 1 in Osteoarthritis of the Knee," *Annals of the Rheumatic Diseases*, 1993, pp. 229-231, vol. 52.

Ramanathan-Girish et al., "Joint Tissue Distribution in Dogs Following Intraarticular (IA) Administration of Recombinant Human Insulin-Like Growth Factor (rhIGF-I)," Absrtract T3416, American Association of Pharmaceutical Scientists Annual Meeting and Exposition, Oct. 21-25, 2001, Denver, Colorado.

Rogachefsky et al., "Treatment of Canine Osteoarthritis with Insulin-Like Growth Factor-1 (IGF-I) and Sodium Pentosan Polysulfate," *Osteoarthritis and Cartilage*, 1993, pp. 105-114, vol. 1.

Trippel, "Growth Factor Actions on Articular Cartilage," *Journal of Rheumatology*, Feb. 1995, pp. 129-132, vol. 22, Supplement 43.

van Beuningen et al., "Insulin-Like Growth Factor Stimulation of Articular Chondrocyte Proteoglycan Synthesis. Availability and Responses at Different Ages," *British Journal of Rheumatology*, 1993, pp. 1037-10430, vol. 32, British Society for Rheumatology.

Wolfgang et al., "Efficacy and Safety of Recombinant Human Insulin-Like Growth Factor (rhIGF-I) in a Canine Model of Osteoarthritis," Abstract B15, Society of Toxicologists Annual Meeting, Mar. 1999, New Orleans, Louisiana.

\* cited by examiner

COMPOSITIONS AND METHODS FOR TREATING ARTICULAR CARTILAGE DISORDERS

CROSS-REFERENCE TO RELATED APPLICATIONS

This application is a continuation of U.S. application Ser. No. 09/285,554, filed Apr. 2, 1999; now abandoned which claims the benefit of U.S. Provisional Application No. 60/080,683, filed Apr. 3, 1998, the contents of which are hereby incorporated herein in their entirety by reference.

FIELD OF THE INVENTION

This invention relates to methods for long-term treatment of mammalian articular cartilage disorders. These methods use therapeutic agents that preserve existing cartilage tissues or stimulate regeneration of cartilage to counteract the degenerative effects of the cartilage disorder or injury.

BACKGROUND OF THE INVENTION

Articular cartilage plays an essential role in the movement of mammalian joints. While synovial fluid within the joint cavity serves as a lubricant, the articular cartilage provides a superior smooth surface between adjacent bones, allowing for near-frictionless motion of joints. It is the articular cartilage that spreads compressive stresses over the articular plate surfaces of the joint, thus protecting weight-bearing bones from shattering.

Articular cartilage is composed of chondrocytes embedded in an extracellular matrix of proteoglycans, collagen, and small molecular weight glycoproteins. Proteoglycans are essential in maintaining strength of the cartilage tissue so that it can withstand compression. Collagen provides the tissue with tensile strength and resistance to shear. In a healthy joint, the extracellular matrix is maintained by a balance between the synthesis and secretion of these macromolecules by chondrocytes and their subsequent degradation by proteolytic enzymes such as proteoglycanases and metalloproteinases, which are also synthesized and secreted by chondrocytes. Damage to the articular surface can disrupt this equilibrium, such that degradation exceeds the ability of chondrocytes to synthesize macromolecules necessary for repair of the cartilage tissues. This disequilibrium results in loss of extracellular matrix or alteration of the material properties of the cartilage tissue. Moreover, with trauma-related injuries, chondrocytes do not regenerate and are incapable of repairing focal defects or cartilage tears. The range of motion for a joint sustaining such an injury can be severely affected.

Chronic disruption of the equilibrium between synthesis and degradation of cartilage matrix macromolecules is associated with the development of osteoarthritis, the most common of the arthritic disorders in humans. As osteoarthritis progresses, the cushioning surface of the affected joint thins as the cartilage softens. Vertical clefts develop, and the integrity of the surface is breached. Cartilage ulcers, appositional bone growth, and osteophytes may appear and restrict movement. When left untreated, continued excessive degradation of proteoglycans and collagens by proteases ultimately leads to total loss of cartilage and eburnation of bone.

Historically, treatment of osteoarthritis and articular cartilage injuries has been limited to pain relief, reduction of joint loading, physical therapy, and orthopedic surgery, all of which are aimed at symptomatic relief rather than treatment of the underlying pathologic disorder. More recently, osteoarthritis research has concentrated on development of "chondroprotective" methods. Such methods involve long-term therapeutic treatment aimed at preserving or stimulating cartilage formation (see Rogachefsky et al. (1993) *Osteoarthritis and Cartilage* 1:105–114; Issebelcher et al. (eds.) *Harrison's Principles of Internal Medicine* (13th ed.; McGraw-Hill Inc., 1994), pp. 1692–1697).

A number of studies have focused on the physiological role of insulin-like growth factor I (IGF-I) on chondrocytes and the generation of extracellular matrix of normal articular cartilage. IGF-I has been shown to stimulate in vitro chondrocyte cell proliferation (see, for example, Osborne et al. (1989) *J. Orthop. Res.* 7: 35–42; and Trippel et al. (1989) *Pediatr. Res.* 25: 76–82), and it stimulates proteoglycan and collagen synthesis by chondrocytes of normal articular cartilage in both in vitro and ex vivo explant studies (see, for example, Guenther et al. (1982) *Experientia* 38: 979–981; Willis and Liberti (1985) *Biochim. Biophys. Acta* 844: 72–80; McQuillan et al. (1986) *Biochem. J.* 240: 423–430; and Tesch et al. (1992) *J. Orthop. Res.* 10: 14–22). These stimulatory actions are mediated through the IGF-I receptor in chondrocyte cells (see Taylor et al. (1988) *FEBS Lett.* 236: 33–38).

Recent studies have examined the physiological function of IGF-I in the etiopathogenesis of osteoarthritis. Expression level of IGF-I apparently increases with the advancement of osteoarthritis pathology (see Middleton and Tyler (1992) *Ann. Rheum. Dis.* 51: 40–447); Middleton et al. (1996) *J. Histochem. Cytochem.* 44: 133–141; and Keyszer et al. (1995) *J. Rheumatology* 22: 275–281). However, articular cartilage responsiveness to IGF-I has been shown to decrease in an experimental arthritis model (see Joosten et al. (1989) *Agents Actions* 26: 193–195). This lack of responsiveness may be associated with decreased synthesis of the IGF-I receptor (see Joosten et al. (1989), increased degradation of IGF-I and/or its receptor (Schalkwijk et al. (1989) *Arthritis Rheum.* 82: 66–71) by extracellular proteolytic enzymes, or by the presence of IGF-I binding proteins at the chondrocyte cell surface or by nonspecific binding of IGF-I to the cartilage matrix thereby blocking access of IGF-I to its receptor sites and negating any potential benefit of increased synthesis of IGF-I and/or its receptor (Dore et al. (1994) *Arthritis and Rheumatism* 37: 253–263).

Parenteral administration of IGF-I has been referred to as a method for enhancing muscle mass of atrophied skeletal muscle in a joint having reduced function due to disease, such as osteoarthritis, or trauma-related injuries (see U.S. Pat. No. 5,444,047).

Recently, IGF-I has been evaluated in vivo for its therapeutic effect in the treatment of osteoarthritis (Rogachefsky et al. (1993) *Osteoarthritis and Cartilage* 1: 105–114). In this study, dogs subjected to anterior cruciate ligament transection were subsequently examined for symptoms of osteoarthritis. Three weeks after transection, 1.0 µg of human recombinant IGF-I was administered intra-articularly 3 times per week for 3 weeks. Results of this study showed that intra-articular administration of IGF-I alone was ineffective in treating osteoarthritis, as cartilage in treated animals was not different from cartilage in untreated animals.

Clearly better methods for treating cartilage disorders or injuries are needed.

SUMMARY OF THE INVENTION

A method for treating mammalian articular cartilage disorders, more particularly osteoarthritis, and trauma-related cartilage injuries using insulin-like growth factor I (IGF-I) as the therapeutic agent is provided. The method of the present invention comprises increasing the total amount of IGF-I present at the site of the articular disorder or injury to a therapeutically effective level that enables maintenance and/or regeneration of cartilage. Increases in the amount of IGF-I at the affected articular site may be obtained via administration of a pharmaceutical composition comprising a therapeutically effective amount of IGF-I. Alternatively, or additionally, the level of naturally produced IGF-I may be regulated by gene therapy or by disruption of IGF-I binding to IGF-I binding proteins, whose binding to IGF-I decreases availability of free IGF-I. The present invention can be used in treating osteoarthritis and trauma-related injuries, wherein cartilage of joints is damaged, by promoting maintenance and/or regeneration of cartilage.

DETAILED DESCRIPTION OF THE INVENTION

Figure 1:
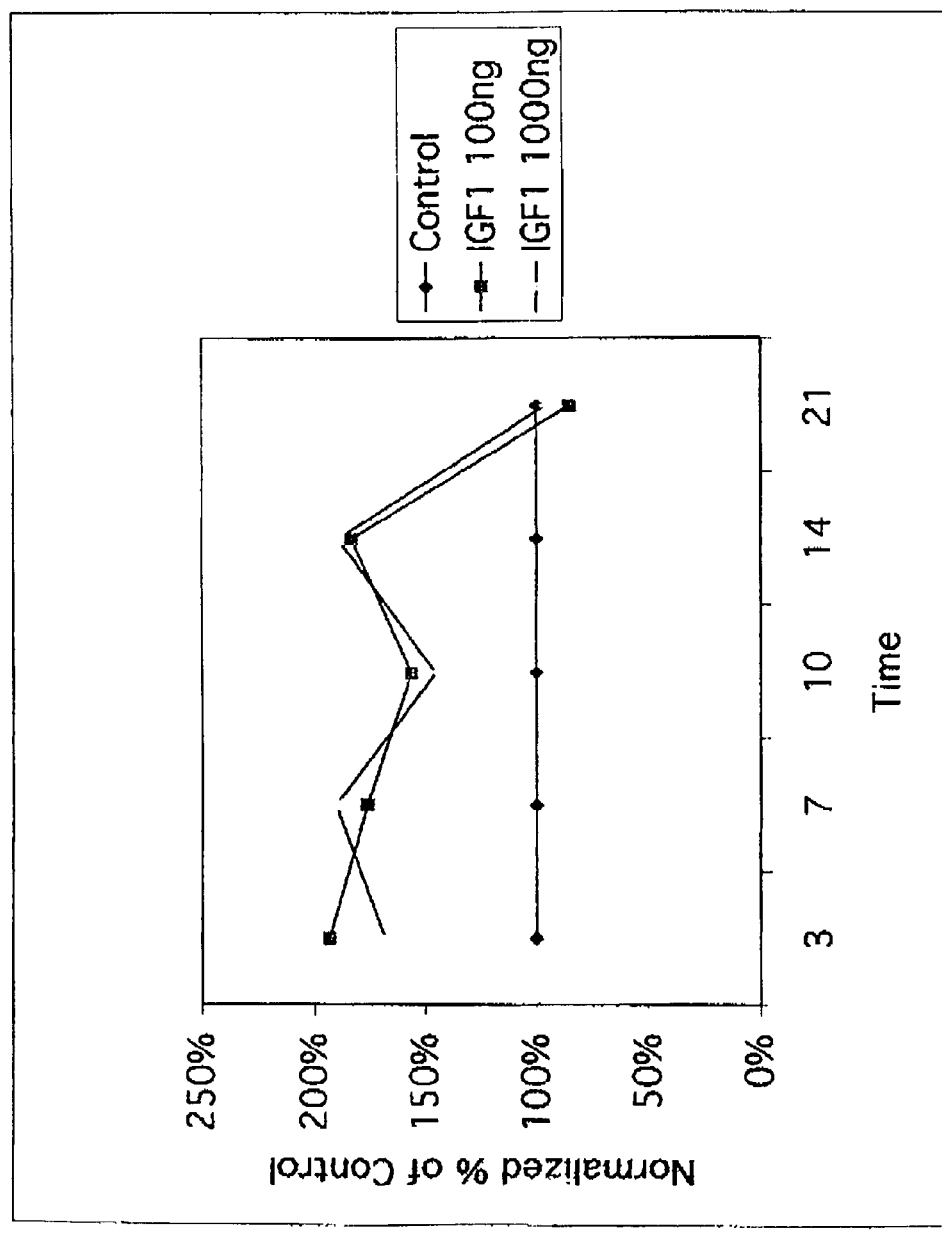
FIG. 1 shows the time course of IGF-I stimulation of proteoglycan synthesis in chondrocytes obtained from a human patient having osteoarthritis.

The present invention relates to a method for treating mammalian articular cartilage disorders, more particularly osteoarthritis, and trauma-related cartilage injuries. This method comprises increasing the total amount of IGF-I present at the diseased or injured articular site to a level that is capable of achieving a desired positive effect on cartilage. By "desired positive effect" is intended the maintenance and/or the regeneration of cartilage. By "maintenance" is intended preservation of cartilage, which encompasses cartilage existing at the onset of treatment and any newly formed cartilage following onset of treatment, including any transplanted chondrocytes or stem cells. By "regeneration" is intended formation of new cartilage, which adds to the existing cartilage at the onset of treatment and which may serve to replace cartilage lost prior to onset of treatment. Maintenance and regeneration of cartilage encompass maintenance and/or regeneration of cartilage components, including, but not limited to, chondrocytes and extracellular matrix molecules. Maintenance and/or regeneration of cartilage is beneficial to the long-term treatment of osteoarthritis and trauma-related injuries to cartilage tissues.

The method of the present invention is effective for long-term treatment of osteoarthritis, a degenerative joint disease wherein a movable synovial-lined joint is eventually rendered nonfunctional. The method can be used for the treatment of localized and generalized idiopathic osteoarthritis, as well as secondary osteoarthritis. Examples of localized idiopathic osteoarthritis include, but are not limited to, afflictions to hands (e.g., Heberden's and Bouchard's nodes, erosive interphalangeal arthritis, and carpal-1st metacarpal), feet (e.g., hallux valgus, hallus rigidus, contracted toes, and talonavicular), knee, hip, shoulder, and spine (e.g., synovial-lined joints of vertebral column, including apophyseal, costovertebral, intervertebral, median atlantoaxial, transitional lumbosacral, and sacroiliac articulations; hyperostosis; Forestier's disease; and diffuse idiopathic skeletal hyperostosis).

Examples of secondary osteoarthritis include, but are not limited to, osteoarthritis caused by or associated with the following underlying problems: acute or chronic trauma-related injuries to articular cartilage, which may be incurred during an occupational or recreational activity; congenital or developmental disorders such as slipped epiphysis, hypermobility syndromes, and bone dysplasias; metabolic disorders such as ochronosis, hemochromatosis, Wilson's disease, and Gaucher's disease; endocrine disorders such as acromegaly, hyperparathyroidism, diabetes mellitus, obesity, and hypothyroidism; calcium deposition diseases such as calcium pyrophosphate dihydrate deposition and apatite arthropathy; and bone and joint diseases such as fractures, avascular necrosis, infection, gout, rheumatoid arthritis, Paget's disease, osteopetrosis, and osteochondritis.

The present invention should be generally applicable to osteoarthritis caused by or associated with all of the above disorders. The disclosed method is also effective for treatment of degenerative disk disease, whereby cartilagenous tissue in the intervertebral disks breaks down. Osteoarthritis and degenerative disk disease are common causes of sustained back pain, and hence the method of the invention provides a means for alleviating this symptom by treatment of the underlying cause.

It will be apparent to those skilled in the art that the method of the present invention can also be used in the treatment of trauma-related articular cartilage injuries, via the same mechanism as for osteoarthritis, i.e., by promoting maintenance and/or regeneration of cartilage. By "trauma-related articular cartilage injuries" is intended damage caused to the chondrocytes, extracellular matrix, or other components of articular cartilage as a result of a traumatic event such that normal joint movement is impaired or is at risk of being adversely affected. Such injuries can be either acute or chronic, and include occupation-related, accident-related, sports-related, or violence-related injuries. When left untreated, serious articular cartilage injuries can eventually lead to development of osteoarthritis.

By "treatment" is intended both therapeutic treatment of an existing articular cartilage disorder, more particularly osteoarthritis, or trauma-related articular cartilage injury, and preventive or prophylactic procedures performed before the occurrence of the disorder or injury. Thus, the mammal to be treated may already have the disorder or injury or may be prone to having the disorder or injury. Risk factors known to predispose an individual to osteoarthritis can be taken into account when determining whether preventive treatment is desirable. For example, it is generally known that the risk of osteoarthritis increases with age and repetitive stress, such as vocational-related stress. It also has been observed that individuals suffering from major joint trauma, obesity, congenital or developmental defects, metabolic or endocrine disorders, and prior inflammatory joint diseases are more prone to osteoarthritis. Thus, it may be desirable to apply the method of the present invention for preventive purposes in these cases.

The method of the present invention may be used with any mammal. Exemplary mammals include, but are not limited to, cats, dogs, horses, cows, sheep, pigs, and more preferably humans.

Increases in the amount of IGF-I at the diseased or injured articular site to a therapeutically effective level may be obtained via administration of a pharmaceutical composition comprising a therapeutically effective dose of IGF-I. By "therapeutically effective dose" is intended a dose of IGF-I that achieves the desired goal of increasing the amount of IGF-I at the articular site to a therapeutically effective level enabling cartilage maintenance and/or regeneration. Such administration may be achieved directly at the site, as with intra-articular injection, or with a delivery system as with sustained release from a biodegradable matrix implanted in proximity to the diseased or injured joint. Alternatively, other modes of administration, such as systemic injections, may be used, as long as they increase the amount of IGF-I at the diseased or injured articular site to a therapeutically effective level that is comparable to that of administering modes that deliver the therapeutically effective dose of IGF-I directly to the diseased or injured articular site.

The term "IGF-I" as used herein refers to insulin-like growth factor I (IGF-I), a single chain peptide having 70 amino acids and a molecular weight of about 7,600 daltons. Insulin-like growth factor I stimulates mitosis and growth processes associated with cell development.

In one embodiment of the invention, increasing in the amount of IGF-I to a therapeutically effective level is achieved via administration of a pharmaceutical composition comprising a therapeutically effect dose. The IGF-I to be administered can be from any animal species including, but not limited to, avian, canine, bovine, porcine, equine, and human. Preferably the IGF-I is from a mammalian species, and more preferably is from a mammal of the same species as the mammal undergoing treatment.

Biologically active variants of IGF-I are also encompassed by the method of the present invention. Such variants should retain IGF-I activities, particularly the ability to bind to IGF-I receptor sites. IGF-I activity may be measured using standard IGF-I bioassays. Representative assays include known radioreceptor assays using placental membranes (see, e.g., U.S. Pat. No. 5,324,639; Hall et al. (1974) *J. Clin. Endocrinol. and Metab.* 39:973–976; and Marshall et al. (1974) *J. Clin. Endocrinol. and Metab.* 39:283–292), a bioassay that measures the ability of the molecule to enhance incorporation of tritiated thymidine, in a dose-dependent manner, into the DNA of BALB/c 3T3 fibroblasts (see, e.g., Tamura et al. (1989) *J. Biol. Chem.* 262:5616–5621), and the like; herein incorporated by reference. Preferably, the variant has at least the same activity as the native molecule.

Suitable biologically active variants can be IGF-I fragments, analogues, and derivatives. By "IGF-I fragment" is intended a protein consisting of only a part of the intact IGF-I sequence and structure, and can be a C-terminal deletion or N-terminal deletion of IGF-I. By "analogue" is intended an analogue of either IGF-I or an IGF-I fragment that comprise a native IGF-I sequence and structure having one or more amino acid substitutions, insertions, or deletions. Peptides having one or more peptoids (peptide mimics) are also encompassed by the term analogue (see International Publication No. WO 91/04282). By "derivative" is intended any suitable modification of IGF-I, IGF-I fragments, or their respective analogues, such as glycosylation, phosphorylation, or other addition of foreign moieties, so long as the IGF-I activity is retained. Methods for making IGF-I fragments, analogues, and derivatives are available in the art. See generally U.S. Pat. Nos. 4,738,921, 5,158,875, and 5,077,276; International Publication Nos. WO 85/00831, WO 92/04363, WO 87/01038, and WO 89/05822; and European Patent Nos. EP 135094, EP 123228, and EP 128733; herein incorporated by reference.

IGF-I variants will generally have at least 70%, preferably 80%, more preferably 85%, even more preferably 90% to 95% or more, and most preferably 98% or more amino acid sequence identity to the amino acid sequence of the reference IGF-I molecule. A variant may, for example, differ by as few as 1 to 10 amino acid residues, such as 6–10, as few as 5, as few as 4, 3, 2, or even 1 amino acid residue.

By "sequence identity" is intended the same amino acid residues are found within the variant sequence and a reference sequence when a specified, contiguous segment of the amino acid sequence of the variant is aligned and compared to the amino acid sequence of the reference sequence. Methods for sequence alignment and for determining identity between sequences are well known in the art. See, for example, Ausubel et al., eds. (1995) *Current Protocols in Molecular Biology*, Chapter 19 (Greene Publishing and Wiley-Interscience, New York); and the ALIGN program (Dayhoff (1978) in *Atlas of Protein Sequence and Structure* 5:Suppl. 3 (National Biomedical Research Foundation, Washington, D.C.). A number of algorithms are available for aligning sequences and determining sequence identity and include, for example, the homology alignment algorithm of Needleman et al. (1970) *J. Mol. Biol.* 48:443; the local homology algorithm of Smith et al. (1981) *Adv. Appl. Math.* 2:482; the search for similarity method of Pearson et al. (1988) *Proc. Natl. Acad. Sci.* 85:2444; the Smith-Waterman algorithm (*Meth. Mol. Biol.* 70:173–187 (1997); and BLASTP, BLASTN, and BLASTX algorithms (see Altschul et al. (1990) *J. Mol. Biol.* 215:403–410). Computerized programs using these algorithms are also available, and include, but are not limited to: GAP, BESTFIT, BLAST, FASTA, and TFASTA, available in the Genetics Computing Group (GCG) package, Version 8, Madison, Wis., USA; and CLUSTAL in the PC/Gene program by Intelligenetics, Mountain View, Calif. Preferably, the sequence identity is determined using the default parameters determined by the program.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will comprise at least 20 contiguous amino acid residues, and may be 30, 40, 50, or more amino acid residues. Corrections for increased sequence identity associated with inclusion of gaps in the variant's amino acid sequence can be made by assigning gap penalties.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Meyers & Miller (1988) *Computer Applic. Biol. Sci.* 4:11–17.

The art provides substantial guidance regarding the preparation and use of such IGF-I variants, as discussed further below. A fragment of IGF-I will generally include at least about 10 contiguous amino acid residues of the full-length molecule, preferably about 15–25 contiguous amino acid residues of the full-length molecule, and most preferably about 20–50 or more contiguous amino acid residues of full-length IGF-I.

Several IGF-I analogues and fragments are known in the art and include those described in, for example, *Proc. Natl. Acad. Sci. USA* 83 (1986) 4904–4907; *Biochem. Biophys. Res. Commun.* 149 (1987) 398–404; *J. Biol. Chem.* 263 (1988) 6233–6239; *Biochem. Biophys. Res. Commun.* 165 (1989) 766–771; Forsbeit et al. (1990) *Biochem. J.* 271: 357–363; U.S. Pat. Nos. 4,876,242 and 5,077,276; and International Publication Nos. WO 87/01038 and WO 89/05822. Representative analogues include one with a deletion of Glu-3 of the mature molecule, analogues with up to 5 amino acids truncated from the N-terminus, an analogue with a truncation of the first 3 N-terminal amino acids (referred to as des(1–3)-IGF-I, des-IGF-I, tIGF-I, or brain IGF), and an analogue including the first 17 amino acids of the B chain of human insulin in place of the first 16 amino acids of human IGF-I.

The IGF-I used in the present invention can be in its substantially purified, native, recombinantly produced, or chemically synthesized forms. IGF-I can be isolated and purified from serum or plasma (see Phillips (1980) *New Eng. J Med.* 302: 371–380, and European Patent No. EP 123, 228). IGF-I can also be chemically synthesized by the solid phase method (see Li et al. (1983) *Proc. Natl. Acad. Sci. USA* 80: 2216–2220). These references are herein incorporated by reference.

Genetic engineering by recombinant DNA techniques can be the most efficient way of producing IGF-I. The human DNA sequence encoding IGF-I is known and can be introduced into host cells for expression. IGF-I can be produced by recombinant DNA techniques in *E. coli*, yeast, insect, and mammalian cells. Secreted IGF-I can be made by adding a signal sequence to the DNA sequence encoding IGF-I. In addition, the DNA sequence encoding IGF-I can be manipulated to make IGF-I fragments, analogues, or derivatives. Such recombinant DNA techniques are generally available in the art. See, for example, International Publication No. WO 96/07424, where recombinant human IGF-I protein is produced in yeast.

The pharmaceutical composition comprising a therapeutically effective dose of IGF-I may contain other components that enhance the therapeutic treatment with IGF-I. Such components include IGF-I binding proteins, IGF-I receptors, and the acid-labile subunit of the IGF-I binding complex. It is generally known that IGF-I action in cartilage is modulated by IGF-I binding proteins, at least six of which (IGFBP-1 through IGFBP-6) have been isolated (see Baxer et al (1989) *Prog. Growth Factors Res.* 1: 49–68; and Rechler et al. (1992) *Growth Regul.* 2: 55–68). Of these, IGFBP-3 is the primary binding protein for IGF-I. Its presence may enhance the stimulatory effect of IGF-I on proteoglycan synthesis (see Chevalier et al. (1996) *British J. Rheumat.* 35: 515–522). In addition, an acid labile glycoprotein also has been shown to be associated with the protein complex formed by IGF-I and its binding proteins. Thus, the therapeutically effective pharmaceutical composition may contain such acid-labile glycoprotein and IGF-I binding proteins, when proven to facilitate the desired effect of IGF-I on cartilage maintenance and/or regeneration. The amount of IGFBPs to be administered with IGF-I can be determined according to the molar ratio between IGF-I and IGFBPs. This molar ratio can range from about 0.5:1 to about 3:1, preferably about 1:1 (see U.S. Pat. No. 5,187,151).

Alternatively, agents that disrupt IGF-I binding to IGFBPs may be effective in increasing the amount of IGF-I present in the diseased or injured articular site to a therapeutically effective level. Thus, the pharmaceutical composition comprising IGF-I may additionally include agents that effectively disrupt formation of the IGF-I-IGFBP binding complex.

The composition may also include other components such as viscosity enhancing agents, such as hyaluronic acid; antioxidants; and stimulants of synovial cells. All such references to components facilitating IGF-I-promoted maintenance and/or regeneration of cartilage are herein incorporated by reference.

In addition to these components, the pharmaceutical composition comprising IGF-I may include one or more protease inhibitors. An exemplary protease inhibitor is sodium pentosan polysulfate (PPS), a polysulfated polysaccharide. This protease inhibitor has efficacy in treating osteoarthritis in combination with low dosages of IGF-I (1 µg IGF-I intra-articularly 3 times per week) (Rogachefsky et al. (1993) *Osteoarthritis and Cartilage* 1: 105–114). Such a protease inhibitor can be administered by other routes, such as intramuscularly, during administration of the effective IGF-I dose.

The pharmaceutical composition in accordance with the present invention may further comprise one or more other therapeutic agents that are effective in treating other disorders in the individual, as long as the biochemical actions of the additional therapeutic agents do not interfere with the efficacy of intended action of the IGF-I treatment. Examples of such agents include, but are not limited to, antibiotics, anti-inflammatory agents, and the like.

A pharmaceutically acceptable carrier should be mixed with the IGF-I and other components in the pharmaceutical composition. By "pharmaceutically acceptable carrier" is intended a carrier that is conventionally used in the art to facilitate the storage, administration, and/or the healing effect of the therapeutic ingredients. A carrier may also reduce any undesirable side effects of the IGF-I. A suitable carrier should be stable, i.e., incapable of reacting with other ingredients in the formulation. It should not produce significant local or systemic adverse effect in recipients at the dosages and concentrations employed for treatment. Such carriers are generally known in the art. Suitable carriers for this invention are those conventionally used large stable macromolecules such as albumin, gelatin, collagen, polysaccharide, monosaccharides, polyvinylpyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), and the like. Slow-release carriers, such as hyaluronic acid, may also be suitable. See particularly Prisell et al. (1992) *Int. J. Pharmaceu.* 85:51–56 and U.S. Pat. No. 5,166,331. Inclusion of hyaluronic acid and other polymers may have an additional beneficial effect on osteoarthritis. See particularly Bragantini (1987) *Clin. Trials J.* 24(4):333–340; Dougados et al. (1993) *Osteoarthritis and Cartilage* 1:97–103; and Lussier et al. (1996) *J. Rheum.* 23:1579–1585; herein incorporated by reference. Other acceptable components in the composition include, but are not limited to, buffers that enhance isotonicity such as water, saline, phosphate, citrate, succinate, acetic acid, and other organic acids or their salts.

Preferred pharmaceutical compositions may incorporate buffers having reduced local pain and irritation resulting from injection of IGF-I compositions. Such buffers include, but are not limited to, low phosphate buffers and succinate buffers. For example, International Publication No. WO 94/15584 describes isotonic IGF-I solution at pH 5.5 to 6.5 with phosphate buffer present in an amount less than 50 mmol/L, which are reported to result in reduced pain upon injection. As another example, the pharmaceutical composition may comprise a succinate buffer with pH in the range of about 4.0 to about 7.5, and succinate in the range of 0.5 mM up to about 100 mM, preferably a range less than about 50 mM, as in the formulation disclosed in the copending application entitled "*Injectible Formulation Containing Suc-* cinate," U.S. patent application Se. No. 60/080,008, filed Apr. 3, 1998. In one embodiment, the IGF-I pharmaceutical composition may be formulated in a 10 mM sodium succinate buffer, pH 6.0, sodium chloride solution.

The pharmaceutical composition may additionally comprise a solubilizing compound, which for purposes of the present invention refers to a compound that includes a guanidinium group and that is capable of enhancing the solubility of IGF-I or an IGF-I analogue. Examples of such solubilizing compounds include the amino acid arginine, as well as amino acid analogs of arginine that retain the ability to enhance solubility of IGF-I at pH 5.5 or greater. Such analogs include, without limitation, dipeptides and tripeptides that contain arginine. By "enhancing the solubility" of IGF-I is intended increasing the amount of IGF-I that can be dissolved in solution at pH 5.5 or greater in the presence of a guanidinium-containing compound compared to the amount of IGF-I that can be dissolved at pH 5.5 or greater in a solution with the same components but lacking the guanidinium-containing compound. The ability of a guanidinium-containing compound to enhance the solubility of IGF-I can be determined using methods well known in the art. In general, the concentration of the solubilizing compound present in the composition will be from about 10 mM to about 1 M, and, for example, in the case of the compound arginine, in a concentration range of about 20 mM to about 200 mM, as disclosed in the copending application entitled "*Compositions Providing for Increased IGF-I Solubility*," U.S. patent application Ser. No. 09/188,051, filed Nov. 6, 1998.

For the purposes of this invention, the pharmaceutical composition comprising IGF-I should be formulated in a unit dosage and in an injectable or infusible form such as solution, suspension, or emulsion. It can also be in the form of lyophilized powder, which can be converted into solution, suspension, or emulsion before administration. The pharmaceutical composition having IGF-I is preferably sterilized by membrane filtration and is stored in unit-dose or multi-dose containers such as sealed vials or ampules.

The method for formulating a pharmaceutical composition is generally known in the art. A thorough discussion of formulation and selection of pharmaceutically acceptable carriers, stabilizers, and isomolytes can be found in *Remington's Pharmaceutical Sciences* (18$^{th}$ ed.; Mack Publishing Company, Eaton, Pa., 1990), herein incorporated by reference.

The IGF-I of the present invention can also be formulated in a sustained-release form to prolong the presence of the pharmaceutically active IGF-I in the treated mammal, generally for longer than one day. Many methods of preparation of a sustained-release formulation are known in the art and are disclosed in *Remington's Pharmaceutical Sciences* (18$^{th}$ ed.; Mack Publishing Company, Eaton, Pa., 1990), herein incorporated by reference. Generally, the IGF-I can be entrapped in semipermeable matrices of solid hydrophobic polymers. The matrices can be shaped into films or microcapsules. Examples of such matrices include, but are not limited to, polyesters, copolymers of L-glutamic acid and gamma ethyl-L-glutamate (Sidman et al. (1983) *Biopolymers* 22: 547–556), polylactides (U.S. Pat. No. 3,773,919 and EP 58,481), polylactate polyglycolate (PLGA) such as polylactide-co-glycolide (see, for example, U.S. Pat. Nos. 4,767,628 and 5,654,008), hydrogels (see, for example, Langer et al. (1981) *J. Biomed. Mater. Res.* 15: 167–277; Langer (1982) *Chem. Tech.* 12: 98–105; and non-degradable ethylene-vinyl acetate, degradable lactic acid-glycolic acid copolyers such as the Lupron Depot™, poly-D-(-)-3-hydroxybutyric acid (EP 133,988), and hyaluronic acid gels (see, for example, U.S. Pat. No. 4,636,524). Suitable microcapsules can also include hydroxymethylcellulose or gelatin-microcapsules and polymethyl methacrylate microcapsules prepared by coacervation techniques or by interfacial polymerization. In addition, microemulsions or colloidal drug delivery systems such as liposomes and albumin microspheres, may also be used. See *Remington's Pharmaceutical Sciences* (18$^{th}$ ed.; Mack Publishing Company Co., Eaton, Pa., 1990).

One such sustained-release formulation is Depo IGF-I (Depofoam), wherein recombinant human IGF-I is encapsulated in multivesicular liposomes, as disclosed in the copending application entitled "High and Low Load Formulations of IGF-I in Multivesicular Liposomes," U.S. patent application Ser. No. 08/925,531, filed Sep. 8, 1997, herein incorporated by reference. The mean residence time of IGF-I in the joint is approximately two-fold longer with Depo IGF-I than with free IGF-I (8.4 hours versus 4.1 hours, respectively). By "residence time" is intended the amount of time during which the concentration of IGF-I remains high enough above baseline to be therapeutically effective. See also the copending application entitled "*Method for Producing Sustained-release Formulations*," U.S. patent application Ser. No. 09/187,780, filed Nov. 6, 1998, wherein IGF-I is encapsulated in PLGA microspheres, herein incorporated by reference.

The method for treating articular cartilage disorders comprising administering a pharmaceutical composition containing a therapeutically effective dose of IGF-I is based on the unexpected discovery that a sufficiently high dose of IGF-I alone is effective in promoting cartilage maintenance and/or regeneration in vivo. Thus, concentration of IGF-I in an administered dose in accordance with the present invention is effective in the treatment of articular cartilage disorders, particularly osteoarthritis, and trauma-related cartilage injuries.

According to this embodiment of the invention, the total amount of pharmaceutically effective IGF-I administered per dose per joint should be in the range of at least about 0.002 mg to about 50.0 mg, about 0.003 mg to about 45.0 mg, about 0.004 mg to about 40.0 mg, about 0.005 mg to about 35.0 mg, about 0.01 mg to about 30.0 mg, preferably about 0.10 mg to about 20.0 mg, more preferably about 0.50 mg to about 10.0 mg, still more preferably about 1.0 mg to about 10.0 mg, even more preferably about 2.0 mg to about 10.0 mg, still more preferably about 1.0 mg to about 5.0 mg, most preferably about 2.0 mg to about 5.0 mg per intraarticular injection. In some regimens, the total amount of IGF-I administered to a joint to achieve a therapeutically effective dose is about 0.01 mg to about 10.0 mg, including about 0.02, 0.03, 0.04, 0.05, 0.06, 0.07, 0.08, 0.09, 0.10 mg or greater. In other regimens, the total amount of IGF-I administered per dose per joint is about 0.10 mg to about 10.0 mg, including about 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 mg or greater per dose per joint, preferably in the range of about 0.10 mg to about 5.0 mg, more preferably in the range of about 0.20 mg to about 4.0 mg, still more preferably in the range of about 0.30 mg to about 3.0 mg. The pharmaceutical composition having a unit dose of IGF-I can be in the form of solution, suspension, or emulsion. The total volume of one dose of the pharmaceutical composition for one joint can range from about 10 µl to about 10 ml, preferably from about 100 µl to about 5 ml, more preferably from about 0.5 ml to about 2 ml. It is apparent that the suitable volume can vary with factors such as the size of the joint treated and the solubility of the components in the composition.

It is recognized that the total amount of IGF-I administered as a unit dose to a particular joint will depend upon the type of pharmaceutical composition being administered, that is whether the composition is in the form of, for example, a solution, a suspension, an emulsion, or a sustained-release formulation. For example, where the pharmaceutical composition comprising a therapeutically effective amount of IGF-I is a sustained-release formulation, IGF-I is administered at a higher concentration. Thus, using a sustained-release formulation, the amount of IGF-I administered per dose per joint is in the range of about 0.10 mg to about 50.0 mg, about 0.20 mg to about 45.0 mg, about 0.30 mg to about 40.0 mg, about 0.40 mg to about 35.0 mg, about 0.50 mg to about 30.0 mg, about 0.60 mg to about 25.0 mg, about 0.70 mg to about 20.0 mg, about 0.80 mg to about 19.0 mg, about 0.90 mg to about 18.0 mg, about 1.0 mg to about 17.0 mg, including about 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5 mg or greater.

Administration of the therapeutically effective dose of IGF-I may be achieved directly at the site, as with intra-articular injection, or with a sustained-release device or delivery system, such as a biodegradable matrix comprising a therapeutically effective dose, as described below. Alternatively, other modes of administration, such as systemic injections, may be used, as long as they increase the amount of IGF-I at the articular site to a therapeutically effective level that is comparable to that of administering modes that deliver the therapeutically effective dose of IGF-I directly to the diseased or injured articular site.

In one embodiment of the invention, the means of administration of the therapeutically effective dose of IGF-I will result in localized delivery of IGF-I to the area of the affected joint. In this embodiment, the therapeutically effective dose of IGF-I is administered intra-articularly to the mammal needing treatment. By "intra-articularly" is intended direct administration into the cavity enclosing the movable joint having osteoarthritis or other cartilage injuries, so that substantial direct contact between the administered IGF-I and articular cartilage is achieved. This can be done by injection or infusion. A single short-term administration of the therapeutically effective dose of IGI-I is used with each delivery of IGF-I to the affected joint. By "short-term administration" is intended completion of administration of the dose within about 3 hours, preferably within about 1.5 hours. More preferably for this embodiment of the invention, administration of the dose is rapid by direct injection into the affected joint.

In another embodiment of the invention, the pharmaceutical composition comprising the therapeutically effective dose of IGF-I is administered intra-articularly intermittently. By "intermittent administration" is intended administration of a therapeutically effective dose of IGF-I, followed by a time period of discontinuance, which is then followed by another administration of a therapeutically effective dose, and so forth. Administration of the therapeutically effective dose may be achieved in a continuous manner, as for example with a sustained-release formulation, or it may be achieved according to a desired daily dosage regimen, as for example with one, two, three or more injections per day. By "time period of discontinuance" is intended a discontinuing of the continuous sustained-released or daily administration of IGF-I. The time period of discontinuance may be longer or shorter than the period of continuous sustained-release or daily administration. During the time period of discontinuance, the IGF-I level in the synovial fluid is substantially below the maximum level obtained during the treatment. The preferred length of the discontinuance period depends on the concentration of the effective dose and the form of IGF-I used. Where the administration comprises intra-articular injection, the discontinuance period is at least 2 days, preferably is at least 4 days, more preferably is at least 1 week and generally does not exceed a period of 4 weeks. For example, when the effective dose is about 1.0 mg, preferably the IGF-I is administered about once per week, as discussed in the example below. When a sustained-release formulation is used, the discontinuance period must be extended to account for the greater residence time of IGF-I at the site of injury. Alternatively, the frequency of administration of the effective dose of the sustained-release formulation can be decreased accordingly. An intermittent schedule of administration of IGF-I to the diseased or injured joint may continue until the desired therapeutic effect of maintenance and/or regeneration of cartilage, and ultimately treatment of the disorder or injury, is achieved.

In yet another embodiment, intermittent intra-articular administration of the therapeutically effective dose of IGF-I is cyclic. By "cyclic" is intended intermittent administration accompanied by breaks in the administration, with cycles ranging from about 1 month to about 2, 3, 4, 5, or 6 months, more preferably about 3 months to about 6 months. For example, the administration schedule might be intermittent administration of the effective dose of IGF-I by intra-articular injection, wherein a single short-term dose is given once per week for 4 weeks, followed by a break in intermittent administration for a period of 3 months, followed by intermittent administration by intra-articular administration of a single short-term dose given once per week for 4 weeks, followed by a break in intermittent administration for a period of 3 months, and so forth. As another example, a single short-term dose may be given once per week for 2 weeks, followed by a break in intermittent administration for a period of 1 month, followed by a single short-term dose given once per week for 2 weeks, followed by a break in intermittent administration for a period of 1 month, and so forth. A cyclic intermittent schedule of intra-articular administration of IGF-I to the diseased or injured joint may continue until the desired therapeutic effect of maintenance and/or regeneration of cartilage, and ultimately treatment of the disorder or injury, is achieved.

Alternatively, administration of the therapeutically effective dose of IGF-I may be achieved directly at the site with a sustained-release device or delivery system. Such devices are well known in the art (see, for example, U.S. Pat. No. 5,206,023). For example, a biodegradable matrix comprising a therapeutically effective dose of IGF-I in a sustained-release form may be implanted within the diseased or injured joint. Such a device would allow for sustained release of IGF-I such that the level of IGF-I at the diseased or injured articular site is maintained at a therapeutically effective level. As the matrix degrades, the therapeutically effective level of IGF-I promotes maintenance and/or regeneration of cartilage within the afflicted joint.

It should be apparent to a person skilled in the art that variations may be acceptable with respect to the therapeutically effective dose and frequency of the administration of IGF-I in this embodiment of the invention. The amount of the IGF-I administered will be inversely correlated with the frequency of administration. Hence, an increase in the concentration of IGF-I in a single administered dose, or an increase in the mean residence time in the case of a sustained release form of IGF-I, generally will be coupled with a decrease in the frequency of administration.

In the practice of the present invention, additional factors should be taken into consideration when determining the therapeutically effective dose of IGF-I and frequency of its administration. Such factors include, for example, the size of the joint, the area of the surface of the cartilage affected, the severity of the cartilage injury or osteoarthritis, and the age, height, weight, health, and physical condition of the individual to be treated. Generally, a higher dosage is preferred if the joint is larger or the disorder or injury is more severe.

Some minor degree of experimentation may be required to determine the most effective dose and frequency of dose administration, this being well within the capability of one skilled in the art once apprised of the present disclosure.

Thus, the amount of IGF-I present at the site of the articular disorder or injury may be manipulated to a therapeutically effective level via administration of a pharmaceutical composition comprising a therapeutically effective dose of IGF-I. In addition, methods for manipulating the level of naturally produced IGF-I are also encompassed by the present invention. Thus, the level of naturally produced IGF-I may be regulated by gene therapy, whereby production of IGF-I in the diseased or injured articular site is enhanced to a therapeutically effective level. Alternatively, therapeutically effective levels of naturally produced IGF-I may be achieved by disruption of IGF-I binding to IGF-I binding proteins, whose binding to IGF-I decreases availability of free IGF-I, thereby influencing IGF-I's normal physiological role in cartilage maintenance and regeneration.

The interest in gene therapy as a means of treating inherited or acquired diseases has led to the development of methods for transferring genetic information, more particularly for delivering nucleotide sequences encoding human genes using viral-mediated gene transfer systems. Such viral-mediated gene transfer systems enable delivery of desired genetic information, in this case a nucleotide sequence encoding IGF-I, to a selected cell or tissue and its subsequent expression there under the direction of the viral promoter. Viral-mediated gene transfer systems are known in the art. See, for example, U.S. Pat. Nos. 5,707,618; 5,714,353; and 5,672,344. In this manner, increases in the amount of IGF-I to a therapeutically effective level can be achieved in vivo by increasing production of IGF-I.

Efficacy of a particular IGF-I dose for any particular means of administration, including intra-articular injection, release at the site from a sustained release device or delivery system, and systemic injection, or for methods aimed at manipulating the level of naturally produced IGF-I, such as gene therapy and disruption of IGF-I binding to IGF-I binding proteins, may be measured in accordance with their ability to promote the desired positive effect of maintenance and/or regeneration of cartilage within the diseased or injured joint, and ultimately treatment of the articular cartilage disorder or trauma-related injury. For example, efficacy of a particular dosage and dosing schedule, or regimen, for treatment of a disease such as osteoarthritis may be measured based on several variables, including, but not limited to, ability to improve pain and/or function within the diseased joint, to slow structural deterioration within the diseased joint, and/or to delay time to surgical replacement of the diseased joint. Efficacy for improving pain may be measured with any validated pain scale, such as a Likert scale, more preferably a 10 cm VAS measurement. Improvement in an afflicted joint may be measured with any validated knee or hip osteoarthritis function measurement, such as that obtained with the Lequesne knee and hip instruments and with the WOMAC. Structural improvements may be validated with a comparison of baseline and final radiographic scores for joint space narrowing (JSN), such as JSN of an osteoarthritic knee or hip.

The present invention also encompasses a method for monitoring proteoglycan and collagen levels in an articular site. A sample of synovial fluid is withdrawn from a subject, preferably using an 18- or 21-gauge needle. A separate aliquot of the sample is centrifuged to obtain a sediment pellet that is then prepared as a paraffin cell block for further analysis. Methods for preparing such cell blocks are known in the art. See, for example, Bratthauer (1994) *Meth. Mol Biol.* 34:81–87. In one embodiment, the pellet is prepared as a mini-cell block as described in Leung and Bedard (1993) *Mod. Pathol.* 6(5):630–632. The cell block is then sectioned and prepared slides are stained with Safranin O to reveal proteoglycan, and with Picrosirius Red following papain digestion to remove proteoglycan and thus unmask and stain the collagen framework. The slides can then be evaluated and scored for degree of Safranin O staining of the particulate extracellular matrix and of cartilage fragments if identified, and for degree of Picrosirius Red staining of extracellular matrix following papain digestion. The degree of staining is then compared to similarly stained slides obtained from a reference synovial fluid sample.

This synovial-fluid histology method is useful as a means of monitoring effects of a drug therapy on articular cartilage, more particularly for monitoring the effects of a drug therapy on a diseased or injured articular site. It is recognized that the method could be used to monitor therapy of any drug administered to any articular site. Thus, in one embodiment of the invention, this histology method may be used to monitor the effect of IGF-I therapy administered in accordance with the present invention, that is where a therapeutically effective amount of IGF-I is administered to an articular site, resulting in a positive effect on cartilage of that site. In this manner, following administering of IGF-I in accordance with the disclosed method of administration, a sample of synovial fluid can be withdrawn from a treated articular site and analyzed for proteoglycan and collagen structure using the synovial-fluid histology method of the invention.

Additional effects of drug therapy on an articular site can be determined from further analysis of the synovial fluid sample. In this manner, the supernatant obtained from the centrifuged aliquot of synovial fluid sample can be analyzed for viscosity using a Mucin Clot Test. Another aliquot of the synovial fluid sample may be analyzed for crystals using a wet smear technique, and for cell assessment and differential count using a stained smear technique. Such cytology techniques are well known in the art. Thus, in the case of IGF-I therapy, values for viscosity, crystals, cell assessment, and differential count would be similar between synovial fluid collected from a normal articular site and from an afflicted articular site undergoing administration of therapeutically effective doses of IGF-I in accordance with the dosing regimen of the invention.

The following experiments are offered by way of illustration and not by way of limitation.

EXPERIMENTAL

EXAMPLE 1

Use of IGF-I in a Model of Canine Osteoarthritis

A canine study was conducted to evaluate the efficacy and safety of intra-articular administration of recombinant human insulin-like growth factor I (rhIGF-I) and a sustained-release formulation of rhIGF-I, referred to as Depo IGF-I, in a model of canine osteoarthritis (OA).

Fifty-six dogs underwent surgical transection of the right anterior cruciate ligament by the method of Pond and Nuki (*Ann. Rheum. Dis.* 32 (1973):887–888). Such transection induces joint instability, leading to production of erosions in the articular cartilage similar to those seen with human osteoarthritis. The animals were premedicated with atropine (0.02 mg/kg, intramuscular (IM)) and acetylpromazine (0.2 mg/kg, IM) prior to induction of anesthesia. Animals were anesthetized with methohexital (7–12 mg/kg, intravenous (IV)), then intubated and maintained in anesthesia with isoflurane inhalant anesthetic delivered through a volume-regulated respirator. The $ETCO_2$ was maintained within individual physiological ranges. An intravenous catheter was placed in a peripheral vessel for administration of lactated Ringer's solution (10 ml/kg/hr). Procaine/benzamine penicillin G (300,000 IU/4.5 kg, IM) and flunixine meglumine (1 mg/kg, IV) were administered preoperatively.

The animals were placed in lateral recumbency and prepared and draped accordingly for aseptic surgery. An ophthalmic ointment was administered to each eye. The right hind leg was clipped of all hair, up to the midline, and just cranial to the iliac crest. The animal was positioned in left lateral recumbency, and the right hind leg taped to an IV pole to allow its preparation for aseptic surgery. The operative area was cleaned with three alternating scrubs of povidone-iodine scrub solution and 70% isopropyl alcohol, with a final application of povidone-iodine solution that was allowed to dry. The leg was draped accordingly for aseptic surgery.

The joint was exposed through an incision in the lateral intermuscular septum to expose the femur by anterior retraction of the vastus lateralis and posterior retraction of the biceps femoris. Care was taken to not disrupt the tendon of origin of the long digital extensor as it originates from the lateral femoral condyle. The lateral geniculate vessels may have been cauterized during this procedure. The joint capsule was opened, the patella was luxated medially, and the joint held in full flexion. The fat pad and synovium surrounding the anterior cruciate ligament (ACL) were removed in order to identify the cranial tibial ligaments of the lateral and medial menisci, and to facilitate later arthrocentesis. Care was taken to not disrupt these ligaments. The ACL was then incised first from under the medial meniscal ligament, along the tibial plateau, and then from under the lateral meniscal ligament. Its origin was then incised from the medial side of the lateral femoral condyle. The wound was closed in layers, and the skin closed with absorbable suture material in a subcuticular pattern. The dogs were then detubated and returned to their USDA-approved housing units, where they were provided with ample standard laboratory chow and water. Dogs were individually housed in either pens or raised-flooring cages.

As much as possible, the type of housing was similar among groups intended for comparison. All dogs in Groups 6–8 were housed in pens and, with the exception of one Group 1 female dog No. 1101, all Group 1–5 dogs were housed in raised-flooring cases. Raised-flooring cages, specifically designed for large dogs, provided equivalent square footage as the pens and mobility, and activity of the dogs within cages and pens appeared similar. Cages and pens were large enough to allow for free activity all day.

After surgery, flunixine meglumine (1 mg/kg) was administered by subcutaneous injection once daily for 3 days for relief of postoperative discomfort. Beginning the day after surgery, at least once daily, dogs were allowed out of their pens or cages and encouraged to exercise within the study room.

Approximately 4 weeks after surgery, dogs were randomly assigned into eight groups of 4 males and 3 females per group, and given weekly or biweekly intra-articular administrations of rhIGF-I, rhIGF-I placebo, Depo IGF-I, or Depo IGF-I placebo for 13 weeks as indicated in Table 1. IGF-I for use in these experiments was recombinantly produced in the yeast strain *Pichia pastoris* and purified essentially as described in U.S. Pat. Nos. 5,324,639, 5,324,660, and 5,650,496 and International Publication No. WO 96/40776. Following isolation, IGF-I was formulated with arginine using dialysis or diafiltration as follows.

By dialysis, bulk rhIGF-I was placed in dialysis tubing with a molecular weight cutoff of 1,000 to 3,000 daltons and dialyzed against three 20-fold volume changes of formulation buffer containing arginine at a concentration of 50 mM, 10 mM sodium citrate, and 90 mM sodium chloride, pH 6.0. Each 20-fold volume change was dialyzed for not less than 3 hours and preferably more than 12 hours. Dialysis was done at 4° C. or at room temperature.

By diafiltration, bulk IGF-I was diafiltered against 10 volumes of formulation buffer containing arginine using a membrane with a molecular weight cutoff of 1,000 to 3,000 daltons, and diafiltered against three 20-fold volume changes of formulation buffer containing arginine at a concentration of 50 mM, 10 mM sodium citrate, and 90 mM sodium chloride. Diafiltration was performed at 4° C. or at room temperature.

The resulting compositions obtained by either dialysis or diafiltration contained IGF-I at a concentration of about 12 mg/ml.

The sustained-release formulation Depo IGF-I was made in accordance with the methods outlined in detail in the copending application entitled "High and Low Load Formulations of IGF-I in Multivesicular Liposomes," U.S. patent application Ser. No. 08/925,531, filed Sep. 8, 1997, herein incorporated by reference.

TABLE 1

Study Design

| | Number of Animals | | | Dose Level | | | |
|---|---|---|---|---|---|---|---|
| Grp No. | % | & | Substance | (mg) | Dosing Regimen[a] | Route; Dose Volume | Scheduled Euthanasia |
| 1 | 4 | 3 | Depo Placebo | 0 | Weekly for 13 doses; | Intra-articular; 2 mL/joint/dose | Week 17 |
| 2 | 4 | 3 | Depo IGF-I | 1 | | | |
| 3 | 4 | 3 | Depo IGF-I | 10 | Weeks 4–16 | | |
| 4 | 4 | 3 | Depo Placebo | 0 | Every 2 weeks for 6 | Intra-articular; | |

TABLE 1-continued

Study Design

Treatment Administration

| Grp No. | Number of Animals % & | | Substance | Dose Level (mg) | Dosing Regimen[a] | Route; Dose Volume | Scheduled Euthanasia |
|---|---|---|---|---|---|---|---|
| 5 | 4 | 3 | Depo IGF-I | 20 | doses; Weeks 4, 6, 8, 10, 12 and 14 | 4 mL/joint/dose | |
| 6 | 4 | 3 | rhIGF-I Placebo | 0 | Weekly for 13 doses; 1 | Intra-articular; 2 mL/joint/dose | |
| 7 | 4 | 3 | rhIGF-I | 1 | Weeks 4–16 | (1 mL/joint/dose for Group 8 on Weeks 5–16) | |
| 8 | 4 | 3 | rhIGF-I | 5[b] | | | |

[a]All dogs underwent unilateral (right knee) transection of the ACL. The day on which surgery was performed was considered to occur during Week 0, so that Week 4 occurred approximately 28 days after surgery.
[b]Dose for Group 8 on Week 4 was 10 mg rbIGF-I in dose volume of 2 mL/joint/dose.

At week 17, the dogs were euthanized. The joints were dissected and examined by observation and histologic study of the cartilage, articular plate, and synovium. In addition, samples of articular cartilage and subchondral bone were removed for further studies. Paraffin sections were made and stained with H & E, Safranin O, and sirius red. Mankin scores based on the traditional Mankin score criteria (Schedule I) and a modified Mankin score substituting osteophyte values for cartilage as an indicator of disruption of joint structure were recorded. Synovial scores were also recorded according to Schedule II. See Mankin et al. (1971) *Bone and Joint Surgery* 53A:523–537 and Gahunia et al. (1995) *Osteoarthritis and Cartilage* 3:169–180 for details of these scoring schedules.

In scoring histological features, the score was based on the most advanced histological feature observed, even if the feature was only focally present. If any bias was introduced by this methodology, it is a bias for an increased score for disease progression and a bias against therapeutic effectiveness.

The changes in cartilage were further studied using morphometry to assess the structural features of cartilage and lesions within cartilage in Groups 6, 7, and 8. The collagen framework of cartilage was assessed using the Picrosirius Red stain after papain digestion. Pretreatment with papain facilitates loss of proteoglycan thereby unmasking the collagen framework.

The articular collagen was assessed in the superficial layer, the upper perichondronal layer, the deep perichondronal layer, and the uncalcified cartilage adjacent to the tidemark using a semi-quantitative scale devised by Dr. Kenneth Pritzker (Schedule III). Higher scores reflect increased staining for collagen. This is indicative of the matrix changes toward decreased proteoglycan quantity or quality and/or collagen condensation on neoformation. These features are recognized as osteoarthritic changes.

The safety of the test articles was evaluated by performing physical and opthalmic examinations and clinical observations, recording blood pressure and ECG readings, determining body weights and food consumption, monitoring clinical pathology (hematology, coagulation, serum and urine chemistry and urinalysis) parameters, performing comprehensive gross necropsy, determining organ weights and by comprehensive histopathology on all animals. Blood glucose was monitored pre-and post-dosing. Synovial fluid analysis (cell count, differential, protein concentration) was also performed.

Schedule I
Osteoarthritis: Articular Cartilage Histopathologic Features-Scoring Method
Mankin Score I + II + III + IV I. Structure

| | |
|---|---|
| Normal (intact surface) | 0 |
| Surface irregularities | 1 |
| Pannus and surface irregularities | 2 |
| Clefts to transitional layer | 3 |
| Clefts to radial layer/varied regions of cartilage thickening or thinning | 4 |
| Clefts to calcified layer | 5 |
| Complete disorganization | 6 |

II. Cells

| | |
|---|---|
| Normal (1/2 cells/lacuna) | 0 |
| Diffuse/slight hypercellularity | 1 |
| Regions of hypercellularity and cloning | 2 |
| Hypocellularity | 3 |

III. Safranin O Staining

| | |
|---|---|
| Normal (uniformally stained matrix) | 0 |
| Slight reduction particularly superficial layer | 1 |
| Moderate reduction extending up to mid layer | 2 |
| Severe reduction entire cartilage thickness | 3 |
| No dye noted | 4 |

IV. Tidemark Integrity

| | |
|---|---|
| Intact/single intact tidemark | 0 |
| Crossed by vessels/reduplication of tidemark | 1 |

A cumulative score of below 5 is considered normal cartilage.
A cumulative score of 5 and above is considered osteoarthritic cartilage.

Schedule II
Osteoarthritis: Synovial Histopathology Reaction

| | Score | |
|---|---|---|
| Synovial Lining | 0 | Normal |
| | 1 | Synovial Lining Cells 1–2 |
| | 2 | Synovial Lining Cells >2 |
| | 3 | Villous Hyperplasia |
| Edema | 0 | Nil |
| | 1 | Focal |
| | 2 | Focal, Villous and Flat Surface |
| | 3 | Generalized |

-continued

Schedule II
Osteoarthritis: Synovial Histopathology Reaction

| | Score | |
|---|---|---|
| Lymphocytes | 0 | Not Seen |
| | 1 | Scattered |
| | 2 | Aggregates |
| | 3 | Follicules |
| Plasma Cells | 0 | Not Seen |
| | 1 | Scattered |
| | 2 | Aggregates |
| | 3 | Follicules |
| Hemosiderin | 0 | Absent |
| | 1 | Slight |
| | 2 | Moderate |
| | 3 | Abundant |
| Fibrosis | 0 | Nil |
| | 1 | Focal, Villous |
| | 2 | Focal, Villous and Flat Surface |
| | 3 | Generalized |

Schedule III
Assessment of Articular Cartilage Collagen - Scoring Method I. Structural "Intact Cartilage"
   I.1 Superficial Layer
      0 - normal
      1 - slight increase in thickness
      2 - marked increase in thickness
   I.2 Upper Layer Perichondronal Collagen
      0 - normal
      1 - slight increase
      2 - marked increase
      3 - confluence of perichondronal collagen
   I.3 Lower Layer Perichondronal Collagen
      0 - normal
      1 - slight increase
      2 - marked increase
      3 - confluence of perichondronal collagen
   I.4 Collagen Adjacent to Tidemark
      0 - normal
      1 - slight increase
      2 - marked increase
      3 - confluence of perichondronal collagen
II. Osteoarthritic Lesions
   II.1 Collagen Adjacent to Osteoarthritic Fissures (OA lesions only)
      0 - normal
      1 - slight increase
      2 - marked increase
      3 - confluence of perichondronal collagen
      4 - confluence and condensation of perichondronal collagen Safety Results There were no test-article-related effects on food consumption, body weights, physical examination findings, ophthalmic examination findings, electrocardiograms, indirect blood pressures and heart rate, or hematology, serum chemistry (except blood glucose), coagulation profile, urinalysis, urine chemistry, and synovial fluid parameter values. There were no adverse test-article-related macroscopic or microscopic alterations.

Intra-articular administration of 5 mg rhIGF-I weekly, 10 mg Depo IGF-I weekly, or 20 mg Depo IGF-I biweekly was associated with significantly lower blood glucose values at 3 hours post-dosing on virtually all weeks of treatment. The test-article-related hypoglycemia was most pronounced (lowest blood glucose values) in dogs receiving 5 (initially 10) mg rhIGF-I and was associated with delayed recovery from anesthesia and lethargy. Hypoglycemia was managed with feeding of canned food and administration of intravenous dextrose solution as needed.

On the basis of anatomic pathology data, a no observable effect level for systemic toxicity after intra-articular injection was determined to be >10 mg Depo IGF-I weekly, >20 mg Depo IGF-I biweekly, and >5 mg rhIGF-I weekly. However, on the basis of blood glucose values, a no observable effect level for hypoglycemia was determined to be >1 mg for both Depo IGF-I and rhIGF-I weekly. Hypoglycemia is an expected pharmacological effect of rhIGF-I therapy.

Results

The anterior cruciate ligament transection model used in this study produced osteoarthritis in the animals within the time frame of the study. In the untreated control group (Group 6), the lesions observed were most frequent and severe in the tibial plateau with lesser changes observed in the medial femoral condyle inferior, femoral condyle, and femoral trochlear notch areas.

The traditional Mankin scores for the four sections studied are presented in Table 2. Table 3 summarizes the histological features of the cartilage and the articular plate. Table 4 summarizes the histological features of the synovium by synovial score criteria. Reduced Mankin scores were observed in the tibial plateau and the medial femoral condyle inferior sites in dogs receiving 1.0 and 5.0 mg rhIGF-I (Groups 7 and 8). The qualitative and semi-quantitative evidence suggested IGF-I serves principally to increase the proportion of matrix that is rich in proteoglycans. Other effects noted in the IGF-I treated groups included enlargement of the chondrons and alterations in the grouping of chondrocytes. These are suggestive of matrix elaboration.

TABLE 2

Pathology and Laboratory Medicine
Mount Sinai Hospital, Toronto, Canada
Osteoarthritis Histopathology: Modified Mankin Scores
Score Using Cartilage Values (Traditional Mankin Score)

| | Trochlear Notch | | Femoral Condyles Central | | Tibial Plateau | | Medial Femoral Condyle Inferior | |
|---|---|---|---|---|---|---|---|---|
| Group # | Mean | SD(±) | Mean | SD(±) | Mean | SD(±) | Mean | SD(±) |
| 1 | 4.9 | 1.1 | 6.4 | 0.5 | 7.6 | 1.1 | 7.7 | 1.5 |
| 2 | 5.3 | 0.8 | 6.9 | 0.4 | 8.1 | 0.4 | 8.6 | 1.5 |

TABLE 2-continued

Pathology and Laboratory Medicine
Mount Sinai Hospital, Toronto, Canada
Osteoarthritis Histopathology: Modified Mankin Scores
Score Using Cartilage Values (Traditional Mankin Score)

| Group # | Trochlear Notch | | Femoral Condyles Central | | Tibial Plateau | | Medial Femoral Condyle Inferior | |
|---|---|---|---|---|---|---|---|---|
| | Mean | SD($\pm$) | Mean | SD($\pm$) | Mean | SD($\pm$) | Mean | SD($\pm$) |
| 3 | 5.0 | 0.8 | 6.0 | 0.8 | 7.6 | 0.8 | 6.3 | 0.8 |
| 4 | 4.9 | 0.7 | 5.7 | 0.8 | 7.3 | 0.8 | 8.0 | 1.3 |
| 5 | 4.7 | 0.8 | 5.9 | 0.4 | 7.4 | 0.8 | 7.0 | 2.0 |
| 6 | 4.9 | 0.7 | 5.3 | 0.5 | 9.0 | 1.0 | 8.0 | 1.3 |
| 7 | 4.7 | 0.5 | 5.0 | 1.0 | 6.6 | 0.5 | 6.3 | 1.0 |
| 8 | 5.0 | 0.6 | 6.6 | 1.0 | 7.1 | 0.7 | 7.3 | 2.6 |

TABLE 3

Pathology and Laboratory Medicine
Mount Sinai Hospital, Toronto, Canada
Osteoarthritis Histopathology: Mankin Grading Scoresheet

| | Features | | | | | | | |
|---|---|---|---|---|---|---|---|---|
| | 1 Cartilage | | | | 2 Cells | | | |
| Group # | Trochlear Notch | Femoral Condyles Central | Tibial Plateau | Medial Femoral Condyle Inferior | Trochlear Notch | Femoral Condyle Central | Tibial Plateau | Medial Femoral Condyle Inferior |
| 1 | 1.9 | 2 | 2.9 | 2.4 | 1.6 | 2 | 2 | 2.4 |
| 2 | 2 | 2 | 3.1 | 2.9 | 1.6 | 2 | 2 | 2.6 |
| 3 | 2 | 2 | 3 | 2.1 | 1.6 | 2 | 2 | 2 |
| 4 | 2 | 2 | 2.4 | 2.6 | 1.6 | 2 | 2 | 2.6 |
| 5 | 2 | 2 | 2.9 | 2.4 | 2 | 2 | 2 | 2.3 |
| 6 | 2 | 2 | 3.3 | 3 | 1.6 | 2 | 2 | 2.1 |
| 7 | 2 | 2.3 | 2.3 | 1.9 | 2 | 2 | 2 | 2 |

| | Features | | | | | | | |
|---|---|---|---|---|---|---|---|---|
| | 3 Safranin O Metachromatic Stain | | | | 4 Tidemark Integrity | | | |
| Group # | Trochlear Notch | Femoral Condyles Central | Tibial Plateau | Medial Femoral Condyle Inferior | Trochlear Notch | Femoral Condyles Central | Tibial Plateau | Medial Femoral Condyle Inferior |
| 1 | 1.3 | 2 | 1.9 | 1.9 | 0.1 | 0.4 | 0.9 | 1 |
| 2 | 1.6 | 1.9 | 2 | 2.1 | 0.1 | 1 | 1 | 1 |
| 3 | 1.4 | 1.4 | 1.6 | 1.6 | 0 | 0.6 | 1 | 0.6 |
| 4 | 1.3 | 1.4 | 2 | 1.9 | 0 | 0.3 | 0.9 | 1 |
| 5 | 0.6 | 1 | 1.6 | 1.9 | 0.1 | 0.9 | 1 | 0.4 |
| 6 | 1.3 | 0.9 | 2.7 | 2.1 | 0 | 0.4 | 1 | 0.7 |
| 7 | 0.7 | 0.1 | 1.3 | 1.9 | 0 | 0.6 | 1 | 0.6 |

TABLE 4

Pathology and Laboratory Medicine
Mount Sinai Hospital, Toronto, Canada
Synovium: Histologic Features

| | Features | | | | | | | | | | | |
|---|---|---|---|---|---|---|---|---|---|---|---|---|
| | Synovial Lining | | Edema | | Lymphs | | Plasma Cells | | Hemosiderin | | Fibrosis | |
| Group # | Medial | Lateral | Medial | Lateral | Medial | Lateral | Medial | Lateral | Medial | Lateral | Medial | Lateral |
| 1 | 1.6 | 1.9 | 0.4 | 0 | 1.3 | 0.7 | 1.1 | 1.1 | 1 | 0.9 | 1.1 | 1.3 |
| 2 | 3 | 2.1 | 0 | 0.4 | 1.4 | 1 | 1.6 | 1.3 | 1 | 1 | 1 | 1 |
| 3 | 2.4 | 3 | 0 | 0.6 | 1 | 1 | 1.4 | 1.7 | 1.1 | 1 | 1.3 | 1 |
| 4 | 2 | 1.3 | 0 | 0.6 | 1.6 | 0.9 | 1.1 | 1.1 | 1.1 | 1 | 1 | 1 |
| 5 | 2 | 1.4 | 0.1 | 0.1 | 1.1 | 1 | 2 | 1.6 | 1 | 1 | 1 | 1 |

TABLE 4-continued

Pathology and Laboratory Medicine
Mount Sinai Hospital, Toronto, Canada
Synovium: Histologic Features

| | Features | | | | | | | | | | | |
|---|---|---|---|---|---|---|---|---|---|---|---|---|
| | Synovial Lining | | Edema | | Lymphs | | Plasma Cells | | Hemosiderin | | Fibrosis | |
| Group # | Medial | Lateral | Medial | Lateral | Medial | Lateral | Medial | Lateral | Medial | Lateral | Medial | Lateral |
| 6 | 2.9 | 1.3 | 0.1 | 0 | 2.1 | 1 | 1.9 | 1.1 | 1 | 1 | 1 | 1 |
| 7 | 2 | 2.3 | 0.6 | 0 | 1.9 | 1 | 1.4 | 1.3 | 1.3 | 1 | 1 | 1 |
| 8 | 2.7 | 1.7 | 0.4 | 0 | 2.7 | 1.4 | 1.9 | 1.4 | 1.3 | 1 | 1 | 1 |

Preliminary cartilage structural morphometry demonstrated cartilage depth (thickness): tibia>femoral condyle, femoral condyle, inferior, trochlear notch (Tables 5–8). In the tibial plateau, femoral condyle, and trochlear notch, the percent of the cartilage area depleted of proteoglycans was markedly reduced in the treated animals (Groups 7 and 8) compared to controls. This is further reflected in the reduced distance from the surface to the proteoglycan rich matrix observed in Groups 7 and 8 compared to Group 6. Osteoarthritic changes were most evident in the tibial plateau. These observations are further extended to evaluation of the changes within osteoarthritic lesions in which fibrillation or fibrillation plus erosion were absent. In both cases, there was a decrease in the portion of surface and area occupied by these lesions in Groups 7 and 8 compared to Group 6. Further, the distance from the surface to the proteoglycan rich areas within the lesions was also reduced in Groups 7 and 8 compared to Group 6. Moreover, there was less cartilage erosion in the cartilage lesions in Groups 7 and 8 compared to Group 6.

It should be noted that other parameters measured including uncalcified cartilage area and calcified cartilage area were similar amongst the three groups. Further, an indication of disruption of the articular plate namely the percentage of penetration of the calcified cartilage length was similar in all three groups. This latter data indicates that no increase in activation of bone resorption of the subchondral plate could be demonstrated.

Preliminary collagen assessment (Tables 9 and 10) demonstrated that Group 6 (controls) had higher scores than Group 7 or Group 8. Similar to the Safranin O assessment and the cartilage morphometry assessment, collagen of the tibial plateau was more severely affected than the medial femoral condyle inferior>distal femoral condyle>distal trochlear notch. The key observation included the exposure of more perichondronal collagen in the upper layers of Group 6 compared to Groups 7 and 8.

TABLE 5

Pathology and Laboratory Medicine
Mount Sinai Hospital, Toronto, Canada
Osteoarthritis Cartilage Structural Morphometry Assessment
Site: Trochlear Notch
File: TDST4.doc

| I. Intact Cartilage Structural Feature | Group 6 Mean (SD) | Group 7 Mean (SD) | Group 8 Mean (SD) |
|---|---|---|---|
| Areas (sq mm) | | | |
| Uncalcified Cartilage Area | 11.3 (3.0) | 10.7 (1.9) | 10.5 (2.5) |
| % Proteoglycan Depleted Area | 5.8 (1.9) | 3.5 (1.7) | 4.3 (3.4) |
| % Proteoglycan Area | 94.2 (1.9) | 96.5 (1.7) | 95.7 (3.4) |
| Calcified Cartilage Area | 1.3 (0.2) | 1.2 (0.2) | 1.2 (0.2) |
| Lengths (mm) | | | |
| Cartilage Surface Length | 17.9 (1.7) | 16.3 (1.6) | 15.9 (2.0) |
| Calcified Cartilage Base Length | 16.4 (2.5) | 15.7 (1.2) | 15.0 (1.5) |
| % Penetration Calcified Cartilage Length | 12.1 (5.3) | 13.7 (6.3) | 12.0 (3.3) |
| Mean Length of Penetration (μm) | 79.2 (17.7) | 82.8 (22.5) | 89.0 (18.2) |
| # Penetrations of Calcified Cartilage Length | | | |
| Depths (μm) | | | |
| Uncalcified Cartilage Depth | 624.7 (137.6) | 659.8 (132.5) | 667.0 (113.0) |
| Surface to Proteoglycan Depth | 40.2 (8.0) | 48.6 (13.1) | 58.1 (14.8) |
| Calcified Cartilage Depth | 80.0 (8.6) | 84.9 (13.0) | 79.7 (9.7) |

TABLE 5-continued

Pathology and Laboratory Medicine
Mount Sinai Hospital, Toronto, Canada
Osteoarthritis Cartilage Structural Morphometry Assessment
Site: Trochlear Notch
File: TDST4.doc

| II. Lesions Structural Feature | Group 6 Mean (SD) | Group 7 Mean (SD) | Group 8 Mean (SD) |
|---|---|---|---|
| Lesions | | | |
| % Total Lesion Surface Length | | | |
| % Lesion Surface Type I Length | | | |
| % Lesion Surface Type II Length | | | |
| % Lesion Surface Type III Length | | | |
| % Total Lesion Area | | | |
| % Lesion Area Type I | | | |
| % Lesion Area Type II | | | |
| % Lesion Area Type III | | | |
| Surface to Proteoglycan Depth Type II (μm) | | | |
| Surface to Proteoglycan Depth Type III (μm) | | | |
| Erosion Depth Type II (μm) | | | |
| Erosion Depth Type III (μm) | | | |
| Erosion Length Type II (μm) | | | |
| Erosion Length Type III (μm) | | | |
| % Pannus Medial | | 4.6 | 11.1 (7.3) |
| % Pannus Lateral | | 7.0 (3.5) | 10.1 (2.0) |

TABLE 6

Pathology and Laboratory Medicine
Mount Sinai Hospital, Toronto, Canada
Osteoarthritis Cartilage Structural Morphometry Assessment
Site: Femoral Condyles, Central
File: CDST4.doc

| I. Intact Cartilage Structural Feature | Group 6 Mean (SD) | Group 7 Mean (SD) | Group 8 Mean (SD) |
|---|---|---|---|
| Areas (sq mm) | | | |
| Uncalcified Cartilage Area | 23.4 (4.6) | 29.3 (4.8) | 28.6 (6.5) |
| % Proteoglycan Depleted Area | 11.0 (4.7) | 8.0 (1.8) | 7.2 (3.9) |
| % Proteoglycan Area | 89.0 (4.7) | 92.0 (1.8) | 92.8 (3.9) |
| Calcified Cartilage Area | 1.8 (0.6) | 2.2 (0.2) | 2.2 (0.3) |
| Lengths (mm) | | | |
| Cartilage Surface Length | 27.1 (3.7) | 29.9 (2.4) | 30.1 (1.8) |
| Calcified Cartilage Base Length | 23.5 (3.1) | 25.6 (1.8) | 25.3 (0.8) |
| % Penetration Calcified Cartilage Length | 6.8 (2.4) | 7.1 (3.0) | 6.8 (2.0) |
| Mean Length of Penetration (μm) | 74.4 (17.5) | 80.2 (21.6) | 76.9 (14.8) |
| # Penetrations of Calcified Cartilage Length | | | |
| Depths (μm) | | | |
| Uncalcified Cartilage Depth | 880.8 (75.5) | 1020.8 (123.8) | 1024.7 (224.4) |
| Surface to Proteoglycan Depth | 97.4 (32.5) | 86.0 (20.7) | 82.7 (21.1) |
| Calcified Cartilage Depth | 77.4 (11.6) | 81.2 (8.4) | 87.7 (10.9) |

| II. Lesions Structural Feature | Group 6 Mean (SD) | Group 7 Mean (SD) | Group 8 Mean (SD) |
|---|---|---|---|
| Lesions | | | |
| % Total Lesion Surface Length | — (—) | 19.0 (—), | — (—) |
| (n = # of animals) | | n = 1 | |
| % Lesion Surface Type I Length | — (—) | 12.8 (—) | — (—) |
| % Lesion Surface Type II Length | — (—) | 6.2 (—) | — (—) |
| % Lesion Surface Type III Length | — (—) | — (—) | — (—) |
| % Total Lesion Area | — (—) | 18.3 (—) | — (—) |
| % Lesion Area Type I | — (—) | 11.9 (—) | — (—) |
| % Lesion Area Type II | — (—) | 6.4 (—) | — (—) |
| % Lesion Area Type III | — (—) | — (—) | — (—) |
| Surface to Proteoglycan Depth Type II (μm) | — (—) | 65.3 (—) | — (—) |
| Surface to Proteoglycan Depth Type III (μm) | — (—) | — (—) | — (—) |
| Erosion Depth Type II (μm) | — (—) | 87.4 (—) | — (—) |

TABLE 6-continued

Pathology and Laboratory Medicine
Mount Sinai Hospital, Toronto, Canada
Osteoarthritis Cartilage Structural Morphometry Assessment
Site: Femoral Condyles, Central
File: CDST4.doc

| | | | |
|---|---|---|---|
| Erosion Depth Type III (µm) | — (—) | — (—) | — (—) |
| Erosion Length Type II (µm) | — (—) | 1638.2 (—) | — (—) |
| Erosion Length Type III (µm) | — (—) | — (—) | — (—) |
| % Pannus Medial | 6.3 (2.0) | 5.6 (1.0) | 8.1 (4.1) |
| % Pannus Lateral | 3.0 (1.3) | 4.8 (—) | 4.6 (1.6) |

TABLE 7

Pathology and Laboratory Medicine
Mount Sinai Hospital, Toronto, Canada
Osteoarthritis Cartilage Structural Morphometry Assessment
Site: Medial Femoral Condyle, Inferior
File: MFCST4.doc

| I. Intact Cartilage Structural Feature | Group 6 Mean (SD) | Group 7 Mean (SD) | Group 8 Mean (SD) |
|---|---|---|---|
| Areas (sq mm) | | | |
| Uncalcified Cartilage Area | 6.3 (1.3) | 7.2 (1.8) | 7.9 (1.1) |
| % Proteoglycan Depleted Area | 14.8 (9.8) | 12.6 (4.7) | 14.0 (4.3) |
| % Proteoglycan Area | 85.2 (9.8) | 87.4 (4.7) | 86.0 (4.3) |
| Calcified Cartilage Area | 0.6 (0.1) | 0.5 (0.1) | 0.7 (0.2) |
| Lengths (mm) | | | |
| Cartilage Surface Length | 9.8 (0.6) | 10.3 (1.4) | 10.8 (1.2) |
| Calcified Cartilage Base Length | 8.7 (0.5) | 9.1 (1.3) | 9.3 (1.2) |
| % Penetration Calcified Cartilage Length | 8.8 (7.3) | 6.6 (4.7) | 5.0 (3.6) |
| Mean Length of Penetration (µm) | 78.4 (27.4) | 78.8 (13.2) | 69.4 (35.1) |
| # Penetrations of Calcified Cartilage Length | | | |
| Depths (µm) | | | |
| Uncalcified Cartilage Depth | 655.9 (127.6) | 737.8 (159.7) | 804.1 (114.1) |
| Surface to Proteoglycan Depth | 82.6 (39.9) | 71.2 (23.9) | 87.8 (31.8) |
| Calcified Cartilage Depth | 62.5 (9.4) | 56.5 (10.4) | 72.1 (16.4) |

| II. Lesions Structural Feature | Group 6 Mean (SD) | Group 7 Mean (SD) | Group 8 Mean (SD) |
|---|---|---|---|
| Lesions | | | |
| % Total Lesion Surface Length (n = # of animals) | — (—) | 30.9 (—), n = 1 | 12.9 (5.6), n = 4 |
| % Lesion Surface Type I Length | — (—) | 30.9 (—) | 6.1 (—) |
| % Lesion Surface Type II Length | — (—) | — (—) | — (—) |
| % Lesion Surface Type III Length | — (—) | — (—) | 15.2 (4.0) |
| % Total Lesion Area | — (—) | 28.0 (—) | 14.1 (8.4) |
| % Lesion Area Type I | — (—) | 28.0 (—) | 6.3 (—) |
| % Lesion Area Type II | — (—) | — (—) | — (—) |
| % Lesion Area Type III | — (—) | — (—) | 16.7 (8.2) |
| Surface to Proteoglycan Depth Type II (µm) | — (—) | — (—) | — (—) |
| Surface to Proteoglycan Depth Type III (µm) | — (—) | — (—) | 122.0 (59.0) |
| Erosion Depth Type II (µm) | — (—) | — (—) | — (—) |
| Erosion Depth Type III (µm) | — (—) | — (—) | 123.2 (37.9) |
| Erosion Length Type II (µm) | — (—) | — (—) | — (—) |
| Erosion Length Type III (µm) | — (—) | — (—) | 1569.8 (267.0) |
| % Pannus Medial | 15.6 (4.0) | 16.8 (7.1) | 12.6 (3.0) |
| % Pannus Lateral | 10.8 (7.0) | 20.3 (6.4) | 13.5 (11.0) |

TABLE 8

Pathology and Laboratory Medicine
Mount Sinai Hospital, Toronto, Canada
Osteoarthritis Cartilage Structural Morphometry Assessment
Site: Tibial Plateau
File: CPST4.doc

| I. Intact Cartilage Structural Feature | Group 6 Mean (SD) | Group 7 Mean (SD) | Group 8 Mean (SD) |
|---|---|---|---|
| Areas (sq mm) | | | |
| Uncalcified Cartilage Area | 27.5 (6.9) | 30.9 (9.1) | 28.6 (8.3) |
| % Proteoglycan Depleted Area | 11.7 (5.6) | 6.0 (1.6) | 6.9 (1.9) |
| % Proteoglycan Area | 88.3 (5.6) | 94.0 (1.6) | 93.1 (1.9) |
| Calcified Cartilage Area | 2.2 (0.6) | 2.2 (0.7) | 2.1 (0.6) |
| Lengths (mm) | | | |
| Cartilage Surface Length | 25.1 (4.4) | 26.1 (4.6) | 25.1 (3.3) |
| Calcified Cartilage Base Length | 24.8 (4.0) | 26.1 (4.4) | 24.5 (3.5) |
| % Penetration Calcified Cartilage Length | 6.1 (2.1) | 6.0 (3.4) | 6.2 (3.1) |
| Mean Length of Penetration ($\mu$m) | 54.6 (12.7) | 57.5 (7.4) | 58.7 (12.8) |
| # Penetrations of Calcified Cartilage Length | | | |
| Depths ($\mu$m) | | | |
| Uncalcified Cartilage Depth | 1093.6 (212.1) | 1165.1 (142.8) | 1161.2 (241.0) |
| Surface to Proteoglycan Depth | 90.4 (27.6) | 56.8 (15.0) | 64.9 (11.4) |
| Calcified Cartilage Depth | 84.3 (11.3) | 83.2 (11.2) | 80.6 (12.7) |

| II. Lesions Structural Feature | Group 6 Mean (SD) | Group 7 Mean (SD) | Group 8 Mean (SD) |
|---|---|---|---|
| Lesions | | | |
| % Total Lesion Surface Length (n = # of animals) | 15.7 (7.2), n = 6 | 9.9 (7.2), n = 6 | 10.8 (9.0), n = 5 |
| % Lesion Surface Type I Length | 12.3 (6.0) | 7.4 (5.3) | 5.1 (1.3) |
| % Lesion Surface Type II Length | 7.1 (—) | 10.8 (—) | 20.9 (—) |
| % Lesion Surface Type III Length | 12.7 (2.9) | 9.4 (8.7) | 5.9 (1.4) |
| % Total Lesion Area | 16.0 (8.9) | 8.3 (7.0) | 9.9 (6.9) |
| % Lesion Area Type I | 16.0 (7.6) | 7.8 (5.5) | 8.8 (2.7) |
| % Lesion Area Type II | 3.7 (—) | 6.7 (—) | 11.5 (—) |
| % Lesion Area Type III | 9.4 (1.5) | 5.9 (6.0) | 3.9 (1.8) |
| Surface to Proteoglycan Depth Type II ($\mu$m) | 409.4 (—) | 86.7 (—) | 205.8 (—) |
| Surface to Proteoglycan Depth Type III ($\mu$m) | 250.2 (6.7) | 123.0 (59.0) | 129.7 (47.3) |
| Erosion Depth Type II ($\mu$m) | 129.5 (—) | 156.1 (—) | 539.0 (—) |
| Erosion Depth Type III ($\mu$m) | 158.7 (47.9) | 135.1 (103.7) | 80.8 (5.3) |
| Erosion Length Type II ($\mu$m) | 1443.8 (—) | 1813.4 (—) | 2439.6 (—) |
| Erosion Length Type III ($\mu$m) | 1967.7 (749.5) | 1508.7 (656.6) | 1487.5 (362.3) |
| % Pannus Medial | 12.2 (—) | 10.0 (—) | 7.2 (—) |
| % Pannus Lateral | 10.2 (3.7) | — (—) | 7.8 (—) |

TABLE 9

Pathology and Laboratory Medicine
Mount Sinai Hospital, Toronto, Canada
Osteoarthritis Histopathology: Articular
Cartilage Collagen Assessment

| | Total Score | | | | |
|---|---|---|---|---|---|
| Group # | Trochlear Notch | Femoral Condyles Central | Tibial Plateau | Medial Femoral Condyle Inferior | Cumulative Score |
| 1 | | | | | |
| 2 | | | | | |
| 3 | | | | | |
| 4 | | | | | |
| 5 | | | | | |
| 6 | 6.1 ± 0.7 | 6.0 ± 1.0 | 7.4 ± 1.1 | 8.4 ± 1.5 | |
| 7 | 5.7 ± 0.5 | 5.3 ± 1.1 | 6.1 ± 1.5 | 6.4 ± 1.3 | |
| 8 | 4.9 ± 0.9 | 4.7 ± 0.8 | 5.7 ± 1.1 | 6.0 ± 0.8 | |

For collagen changes, the specific osteoarthritic lesions were assessed separately from the cartilage as a whole. The osteoarthritic lesions in Group 6 showed much more collagen condensation (and possibly collagen neoformation) than did the lesions in Group 7 or Group 8. Further, in cartilage subjacent to pannus, which is a known feature of this model, the unmasking of collagen was much greater in Group 6 than in Group 7 and 8.

The synovial reaction was relatively mild with a trend to higher scores in the medial synovial sample. There was very mild synovial cell hyperplasia. The inflammatory cell infiltrate was mixed consisting of lymphocytes and macrophages (Tables 11 and 4).

TABLE 10

Pathology and Laboratory Medicine
Mount Sinai Hospital, Toronto, Canada
Osteoarthritis Histopathology: Articular Cartilage Collagen Assessment

| | Features | | | | | | | |
|---|---|---|---|---|---|---|---|---|
| | Superficial Layer Collagen | | | | Upper Layer Perichondronal Collagen | | | |
| Group # | Trochlear Notch | Femoral Condyles Central | Tibial Plateau | Medial Femoral Condyle Inferior | Trochlear Notch | Femoral Condyles Central | Tibial Plateau | Medial Femoral Condyle Inferior |
| 1 | | | | | | | | |
| 2 | | | | | | | | |
| 3 | | | | | | | | |
| 4 | | | | | | | | |
| 5 | | | | | | | | |
| 6 | 2 | 1.9 ± 0.4 | 2 | 2 | 0 | 1.3 ± 0.8 | 1.1 ± 0.9 | 1.9 ± 1.1 |
| 7 | 1.9 ± 0.4 | 2 | 1.7 ± 0.5 | 1.9 ± 0.4 | 0.1 ± 0.4 | 0.4 ± 0.8 | 0.3 ± 0.8 | 0.7 ± 1.0 |
| 8 | 1.4 ± 0.5 | 2 | 1.6 ± 0.5 | 1.9 ± 0.4 | 0 | 0.1 ± 0.4 | 0 | 0 |

| | Features | | | | | | | |
|---|---|---|---|---|---|---|---|---|
| | Lower Layer Perichondronal Collagen | | | | Deep Layer Collagen | | | |
| Group # | Trochlear Notch | Femoral Condyles Central | Tibial Plateau | Medial Femoral Condyle Inferior | Trochlear Notch | Femoral Condyles Central | Tibial Plateau | Medial Femoral Condyle Inferior |
| 1 | | | | | | | | |
| 2 | | | | | | | | |
| 3 | | | | | | | | |
| 4 | | | | | | | | |
| 5 | | | | | | | | |
| 6 | 2.9 ± 0.4 | 2.1 ± 1.2 | 1.7 ± 0.5 | 2.9 ± 0.4 | 1.3 ± 0.5 | 0.7 ± 1.3 | 2.6 ± 0.5 | 1.7 ± 0.5 |
| 7 | 2.7 ± 0.5 | 2.3 ± 1.1 | 1.6 ± 0.8 | 2.4 ± 1.0 | 1 | 0.6 ± 1.1 | 2.6 ± 0.5 | 1.4 ± 0.8 |
| 8 | 2.4 ± 0.5 | 2.1 ± 0.7 | 1.4 ± 0.5 | 2.6 ± 0.5 | 1 | 0.4 ± 1.1 | 2.7 ± 0.5 | 1.6 ± 0.8 |

TABLE 11

Pathology and Laboratory Medicine
Mount Sinai Hospital, Toronto, Canada
Synovium: Histologic Features

| | Synovium Score | |
|---|---|---|
| Group # | Medial | Lateral |
| 1 | 6.6 | 5.9 |
| 2 | 8.0 | 6.9 |
| 3 | 7.3 | 8.3 |
| 4 | 6.9 | 5.9 |
| 5 | 7.3 | 6.1 |
| 6 | 9.0 | 5.4 |
| 7 | 8.1 | 6.6 |
| 8 | 10.0 | 6.6 |
| Mean Score | 7.9 | 6.4 |

Note:
In all except Group 3, the lateral side has the lower scores.

Discussion

The ACLT model produces sufficient distinctive osteoarthritic lesions to allow discrimination of therapeutic effects between the controls and the test animals. These effects were most readily seen in the tibial plateau. Safranin O stained semi-qualitative assessment by Mankin scoring as well as cartilage structural morphometry indicated that compared to the control group 6, the groups treated with rhIGF-I (Groups 7 and 8) demonstrated less severe lesions and more retention of proteoglycan. The retention of proteoglycan was evident in both the areas of intact cartilage and areas of osteoarthritic lesions which showed fibrillation and erosion.

With regard to the assessment of the collagen framework, more collagen became unmasked in the control group 6 compared to the treated groups (Groups 7 and 8). As the collagen becomes exposed by the proteoglycan depletion by the action of the papain staining, the lack of exposure of collagen reflects the retention of proteoglycans. The retention of proteoglycans may result from either alteration in the proteoglycan composition or an increase in the proteoglycan concentration within the cartilage.

Of great interest were the collagen changes in the osteoarthritic lesions. In the untreated control group 6, the osteoarthritic lesions invariably demonstrated collagen condensation with some evidence for collagen neoformation. In contrast, the treated animals, Groups 7 and 8, had shallower lesions, and very much more variable and less exposure of the collagen. This lack of unmasking of the collagen framework and reduced lesion extent appears to be related to the retention of proteoglycans within the cartilage and to the relative resistance of cartilage proteoglycans to degradation by papain compared to cartilage matrix in Group 6.

Treatment with rhIGF-I also impacted the cellularity of the cartilage. These effects, including chondrocyte relative preservation (decreased loss of chondrocyte density) within the lesions and relative preservation (decreased loss) of chondron density within the lesions, are seen most clearly at sites of structural osteoarthritic lesions. This can be interpreted as a chondroprotective effect (less loss of chondrons and chondrocytes). There is a suggestion for chondroregenerative effects (increased cell density, % clustered chondrons) even in intact cartilage in the test animals.

The synovial reaction was relatively mild and is consistent with repeated intra-articular injections.

Conclusions

The results from the assessment of osteoarthritis using the Mankin scale, the assessment of proteoglycan retention using Safranin O staining, the morphometric assessment of articular cartilage and osteoarthritic lesions, and the semiqualitative scoring of the collagen framework in osteoarthritis all demonstrate that the osteoarthritic lesions are attenuated in the rhIGF-I treated groups (Groups 7 and 8) compared to the control (Group 6). This effect appears to be related to either an increase in proteoglycans or beneficial alteration in proteoglycan composition in the treated groups or a combination of these two factors. Further, rhIGF-I treatment appears to retard or prevent collagen condensation in osteoarthritic lesions. At the very least, these effects are chondroprotective. Additionally, they strongly suggest the possibility of chondroregeneration from this agent.

The histologic and histomorphometric assessment of cartilage also demonstrated that in the cartilage domains unaffected by specific osteoarthritic lesions, the cartilage remained intact comparable to the control animals. Further, there was no increased resorption of bone in the articular plate in the treated animals compared to the controls.

These studies indicate that IGF-I can act as a chondroprotective agent in osteoarthritis principally by acting as an anabolic agent and possibly as an anticatabolic agent for matrix components such as proteoglycans. These data also suggest that IGF-I can act as a chondroregenerative agent. Importantly, no adverse effects of IGF-I were demonstrated by either histology or histomorphometry.

In summary, the data disclosed herein demonstrate clearly that IGF-I could be effective in reducing the severity of osteoarthritis and in stimulating cartilage repair to a significant degree, but at higher doses than had previously been known. IGF-I treatment in the methods disclosed above proved that Group 3 (10 mg/week of Depo IGF-I), Group 7 (1 mg/week of rhIGF-1), and Group 8 (5 mg/week of rhIGF-I) showed definite positive therapeutic effects. In addition, Group 5 (20 mg of Depo IGF-I biweekly) also showed some positive therapeutic effects as reflected in the lower Mankin scores in this group. The safety data, including macroscopic and microscopic pathology, indicated the doses of rhIGF-I described in the dog study were well tolerated. Hypoglycemia, a known pharmacological effect of rhIGF-I, was the only adverse event observed, and this effect can be easily monitored and managed.

EXAMPLE 2

IGF-I Stimulation of Proteoglycan in Cell Culture

Chondrocytes were obtained from a human with osteoarthritis. Cells in suspension (alginate beads) were exposed to 100 ng/ml or 1,000 ng/ml rhIGF-I for 10 days. The IGF-I response ($^{35}$S incorporation into proteoglycan) was assessed on days 3, 7, and 10. rhIGF-I was then removed from the media, and the IGF-I response was assessed again on days 14 and 21. Proteoglycan was measured in the media, the cell pellet, and in the alginate.

The subject's cells showed IGF-I stimulation of proteoglycan synthesis during the first 10 days as compared to the control cells, which were not exposed to rhIGF-I (FIG. 1). Further, chondrocytes continued to demonstrate enhanced proteoglycan synthesis from day 10 to day 14, four days after removal of IGF-I. These data provide additional evidence for the benefit of intermittent dosing in the treatment of osteoarthritis.

Although the foregoing invention has been described in some detail by way of illustration and example for purposes of clarity of understanding, it will be apparent that certain changes and modifications may be practiced within the scope of the appended claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. A method for promoting a desired positive effect on cartilage of a diseased or injured articular site in a mammal, said method comprising increasing IGF-I at said articular site to a therapeutically effective level that is capable of promoting said positive effect, wherein said increasing is achieved by delivering to said articular site a therapeutically effective dose of human IGF-I or biologically active variant thereof, wherein said dose is about 0.01 mg to about 50.0 mg, wherein said variant is a polypeptide having IGF-I activity and having at least 70% sequence identity to the amino acid sequence of said human IGF-I, and wherein said IGF-I activity is stimulation of proteoglycan synthesis.

2. The method of claim 1, wherein said method comprises administering said therapeutically effective dose directly to said articular site.

3. The method of claim 2, wherein said administering is by intra-articular injection.

4. The method of claim 3, wherein said mammal is a human and wherein human IGF-I is administered.

5. The method of claim 4, wherein said human IGF-I is recombinant human IGF-I.

6. The method of claim 2, wherein said therapeutically effective dose of human IGF-I or variant thereof is administered intermittently.

7. The method of claim 6, wherein said intermittent administration comprises an administration of a pharmaceutical composition comprising said therapeutically effective dose of human IGF-I or variant thereof followed by a time period of discontinuance, wherein said period of discontinuance is longer than the residence time of said pharmaceutical composition at said site, and repetition of the pattern of administration followed by discontinuance for as long as necessary to achieve said positive effect on said cartilage.

8. The method of claim 7, wherein said therapeutically effective dose of human IGF-I or variant thereof is selected from the group consisting of 0.3 mg, 1.0 mg, and 3.0 mg.

9. The method of claim 7, wherein said human IGF-I or variant thereof is administered as a sustained-release formulation.

10. The method of claim 7, wherein said pharmaceutical composition is administered by intra-articular injection.

11. The method of claim 10, wherein said mammal is a human and wherein human IGF-I is administered.

12. The method of claim 11, wherein said human IGF-I is recombinant human IGF-I.

13. The method of claim 1, wherein said therapeutically effective dose of human IGF-I or variant thereof is about 0.1 mg to about 20.0 mg.

14. A method for treating an articular cartilage disorder at an articular site in a mammal comprising increasing IGF-I at said articular site to a therapeutically effective level that is capable of promoting a desired positive effect on cartilage of said articular site, wherein said increasing is achieved by delivering to said articular site a therapeutically effective dose of human IGF-I or biologically active variant thereof, wherein said dose is about 0.01 mg to about 50.0 mg, wherein said variant is a polypeptide having IGF-I activity and having at least 70% sequence identity to the amino acid sequence of said human IGF-I, and wherein said IGF-I activity is stimulation of proteoglycan synthesis.

15. The method of claim 14, wherein said method comprises administering said therapeutically effective dose directly to said articular site.

16. The method of claim 15, wherein said administering is by intra-articular injection.

17. The method of claim 16, wherein said articular cartilage disorder is osteoarthritis.

18. The method of claim 16, wherein said articular cartilage disorder results from a trauma-related injury.

19. The method of claim 17, wherein said therapeutically effective dose of human IGF-I or variant thereof is administered intermittently.

20. The method of claim 19, wherein said intermittent administration comprises an administration of a pharmaceutical composition comprising said therapeutically effective dose of human IGF-I or variant thereof followed by a time period of discontinuance, wherein said period of discontinuance is longer than the residence time of said pharmaceutical composition at said site, and repetition of the pattern of administration followed by discontinuance for as long as necessary to achieve said treatment of osteoarthritis.

21. The method of claim 20, wherein said therapeutically effective dose of human IGF-I or variant thereof is selected from the group consisting of 0.3 mg, 1.0 mg, and 3.0 mg.

22. The method of claim 20, wherein said human IGF-I or variant thereof is administered as a sustained-release formulation.

23. The method of claim 20, wherein said mammal is a human and wherein human IGF-I is administered.

24. The method of claim 23, wherein said human IGF-I is recombinant human IGF-I.

25. The method of claim 16, wherein said mammal is a human and wherein human IGF-I is administered.

26. The method of claim 25, wherein said human IGF-I is recombinant human IGF-I.

27. The method of claim 15, wherein said therapeutically effective dose of human IGF-I or variant thereof is administered intermittently.

28. The method of claim 27, wherein said intermittent administration comprises an administration of a pharmaceutical composition comprising said therapeutically effective dose of human IGF-I or variant thereof followed by a time period of discontinuance, wherein said period of discontinuance is longer than the residence time of said pharmaceutical composition at said site, and repetition of the pattern of administration followed by discontinuance for as long as necessary to achieve said treatment of said articular cartilage disorder.

29. The method of claim 28, wherein said therapeutically effective dose of human IGF-I or variant thereof is selected from the group consisting of 0.3 mg, 1.0 mg, and 3.0 mg.

30. The method of claim 28, wherein said human IGF-I or variant thereof is administered as a sustained-release formulation.

31. The method of claim 28, wherein said pharmaceutical composition is administered by intra-articular injection.

32. The method of claim 31, wherein said mammal is a human and wherein human IGF-I is administered.

33. The method of claim 32, wherein said human IGF-I is recombinant human IGF-I.

34. The method of claim 14, wherein said therapeutically effective dose of human IGF-I or variant thereof is about 0.1 mg to about 20.0 mg.

35. The method of claim 18, wherein said therapeutically effective dose of human IGF-I or variant thereof is administered intermittently.

36. The method of claim 35, wherein said intermittent administration comprises an administration of a pharmaceutical composition comprising said therapeutically effective dose of human IGF-I or variant thereof followed by a time period of discontinuance, wherein said period of discontinuance is longer than the residence time of said pharmaceutical composition at said site, and repetition of the pattern of administration followed by discontinuance for as long as necessary to achieve said treatment of said trauma-related injury.

37. The method of claim 36, wherein said therapeutically effective dose of human IGF-I or variant thereof is selected from the group consisting of 0.3 mg, 1.0 mg, and 3.0 mg.

38. The method of claim 36, wherein said human IGF-I or variant thereof is administered as a sustained-release formulation.

39. The method of claim 36, wherein said mammal is a human and wherein human IGF-I is administered.

40. The method of claim 39, wherein said human IGF-I is recombinant human IGF-I.

* * * * *